United States Patent [19]

Roskam et al.

[11] Patent Number: 5,417,970

[45] Date of Patent: May 23, 1995

[54] DRUGS CONTAINING A GLYCOSYLATED INTERLEUKIN-2

[75] Inventors: Willem Roskam, deceased, late of Montgiscard, by Nicole Brunot, legal representative; Bertrand Basuyaux, Courbevoie; Pascual Ferrara, Villefranche de Lauragais; Martine Laporte, Ramonville Saint-Agne; Thierry Maureaud, Auzielle; Natalio Vita, Toulouse; Alain Bayol, Tournefeuille; Geneviéve Perry, Toulouse, all of France

[73] Assignee: Sanofi, Paris, France

[21] Appl. No.: 152,886

[22] Filed: Nov. 16, 1993

Related U.S. Application Data

[63] Continuation of Ser. No. 715,862, Jun. 17, 1991, abandoned, which is a continuation of Ser. No. 499,472, Jun. 21, 1990, abandoned.

[30] Foreign Application Priority Data

Oct. 21, 1988 [FR] France ................ 88 13865
Oct. 21, 1988 [FR] France ................ 89 05150

[51] Int. Cl.$^6$ .................. A61K 37/02; C07K 3/20; C07K 3/22; C07K 15/14
[52] U.S. Cl. .................. 424/85.2; 435/69.52; 530/351; 530/416; 530/417
[58] Field of Search .............. 530/351, 412, 416, 417; 435/69.12, 71.1, 72.85; 424/85.2; 514/12, 801

[56] References Cited

U.S. PATENT DOCUMENTS

| | | | |
|---|---|---|---|
| 3,024,167 | 3/1962 | Damaskus | 514/801 |
| 4,490,289 | 12/1984 | Stern | 530/351 |
| 4,675,383 | 6/1987 | Bohlen et al. | 520/351 |
| 4,778,879 | 10/1988 | Mertelsmann et al. | 530/351 |
| 5,217,881 | 6/1993 | Park | 436/546 |

FOREIGN PATENT DOCUMENTS 0158487 10/1985 European Pat. Off. .
0172619 2/1986 European Pat. Off. .
0307285 3/1989 .
WO88/00967 2/1988 WIPO .

OTHER PUBLICATIONS

Olden et al., *Function of Glycoprotein Glycans,* TIBS, Feb. 1985.
Conradt, et al., *Structures of the major carbohydrates of natural human interleukin-2,* Eur. J. Biochem, 153:255-261 (1986), pp. 255-261.
Conradt, et al, Biochemical and Biophysical Research Communications, vol. 150, No. 1, Jan. 15, 1988, pp. 97-103.
R. J. Bobb, Immunology Today, 5:203-209 (1984).
Conradt et al, Eur. J. Biochem. 153:255-261 (1985).
Ferrara et al, FEBS Letters 226(1):47-52(1987).
K. Kato et al., Biochem. and Biphys. Commun. 127(1):182-190 (1985).
M. P. Weir, et al., J. of Chromatograhy 396:209-215 (1987).
Robb et al, Proc. Nat'l Acad. Sci. USA 81:6486-6490 (1984).
Krigel et al., Cancer Res. 48:3875-3881.
Krigel et al., Cancer Res. 48:3875-3881 (1988).
Allegretta et al., J. of Clin. Immunol. 6:481-490 (1986).
Waldmann et al., J. Exp. Med. 160: 1450-1466 (1984).
Rosenstein et al, J. Immunol. 137:1735-1742 (1986).
S. E. Ettinghausen, J. Nat'l. Cancer Inst. 80(3):177-188 (1988).
Robert K. Scopes, "Protein Purification, Principles and Practices" (2d ed. 1987) pp. 218-220.

*Primary Examiner*—Jeffrey E. Russel
*Attorney, Agent, or Firm*—Foley & Lardner

[57] ABSTRACT

An interleukin-2 preparation suitable for pharmaceutical purposes, consisting essentially of disialilated glycosylated interleukin-2, monosialilated glycosylated interleukin-2, or a mixture thereof, and substantially free of organic solvents, is isolated from recombinant CHO cells transformed with a vector containing a DNA sequence coding for a natural precursor of human interleukin-2, and is purified by a multi-step process.

25 Claims, 9 Drawing Sheets

ELECTROPHORESIS ON POLYACRYLAMIDE GEL IN THE PRESENCE OF SDS AFTER REDUCTION OF SAMPLES.
DYEING WITH SILVER

1 MIXTURE OF THE FOUR FORMS OF IL-2
2 PRODUCT OBTAINED AT THE END OF STEP 2d) IN EXAMPLE 5
3 IL2N2
4 IL2N1
5 MOLECULAR WEIGHT MARKER
6 DITTO 3
7 DITTO 5

ELECTROPHORESIS ON POLYACRYLAMIDE GEL IN THE PRESENCE OF SDS AFTER REDUCTION OF SAMPLES. DYEING WITH SILVER

| | |
|---|---|
| 1 | MIXTURE OF THE FOUR FORMS OF IL-2 |
| 2 | PRODUCT OBTAINED AT THE END OF STEP 2d) IN EXAMPLE 5 |
| 3 | IL2N2 |
| 4 | IL2N1 |
| 5 | MOLECULAR WEIGHT MARKER |
| 6 | DITTO 1 |
| 7 | DITTO 5 |

ANALYSIS BY HPLC ON REVERSE PHASE COLUMN OF THE PRODUCT OBTAINED AT THE END OF STEP 2d) IN EXAMPLE 5.

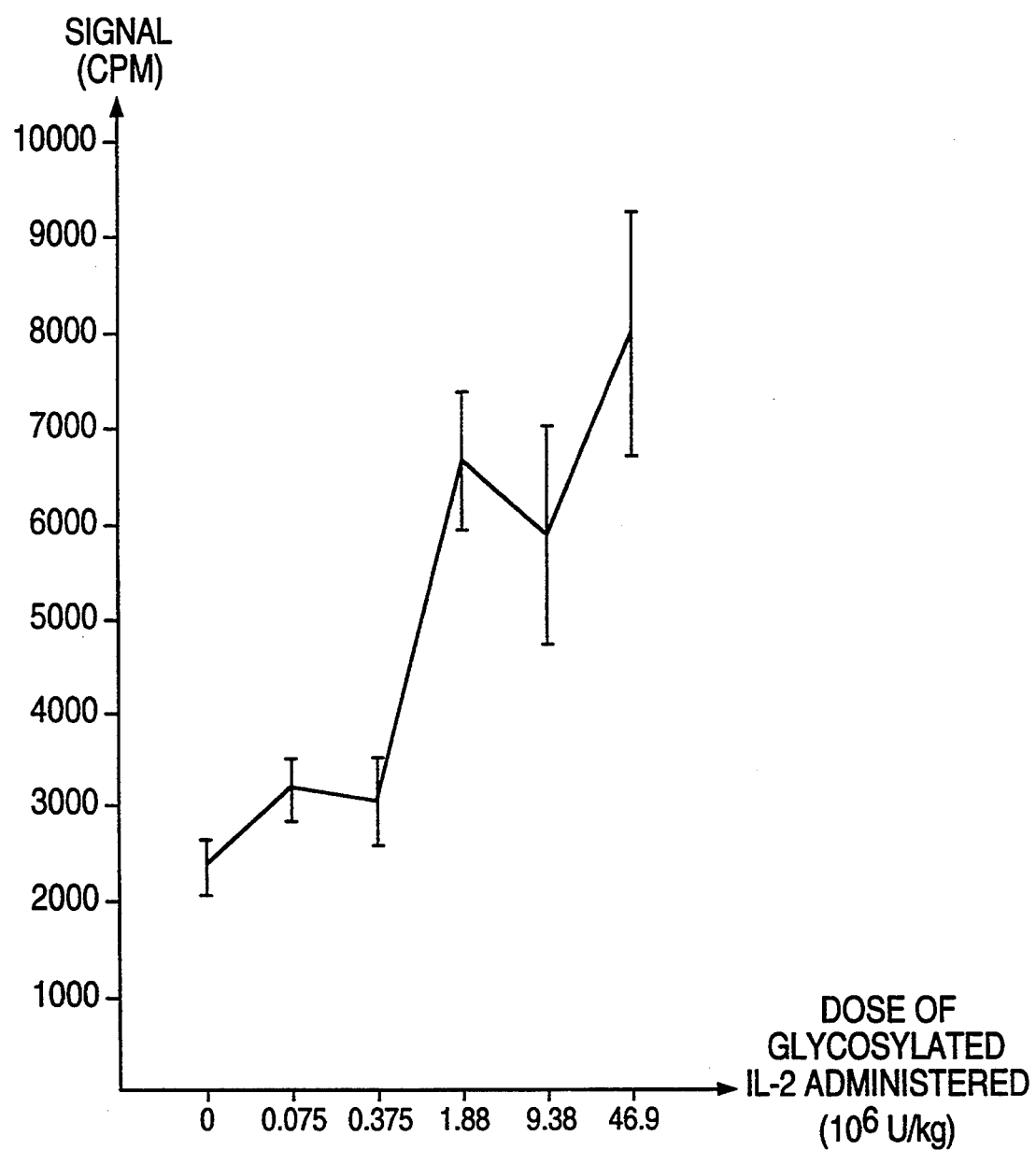

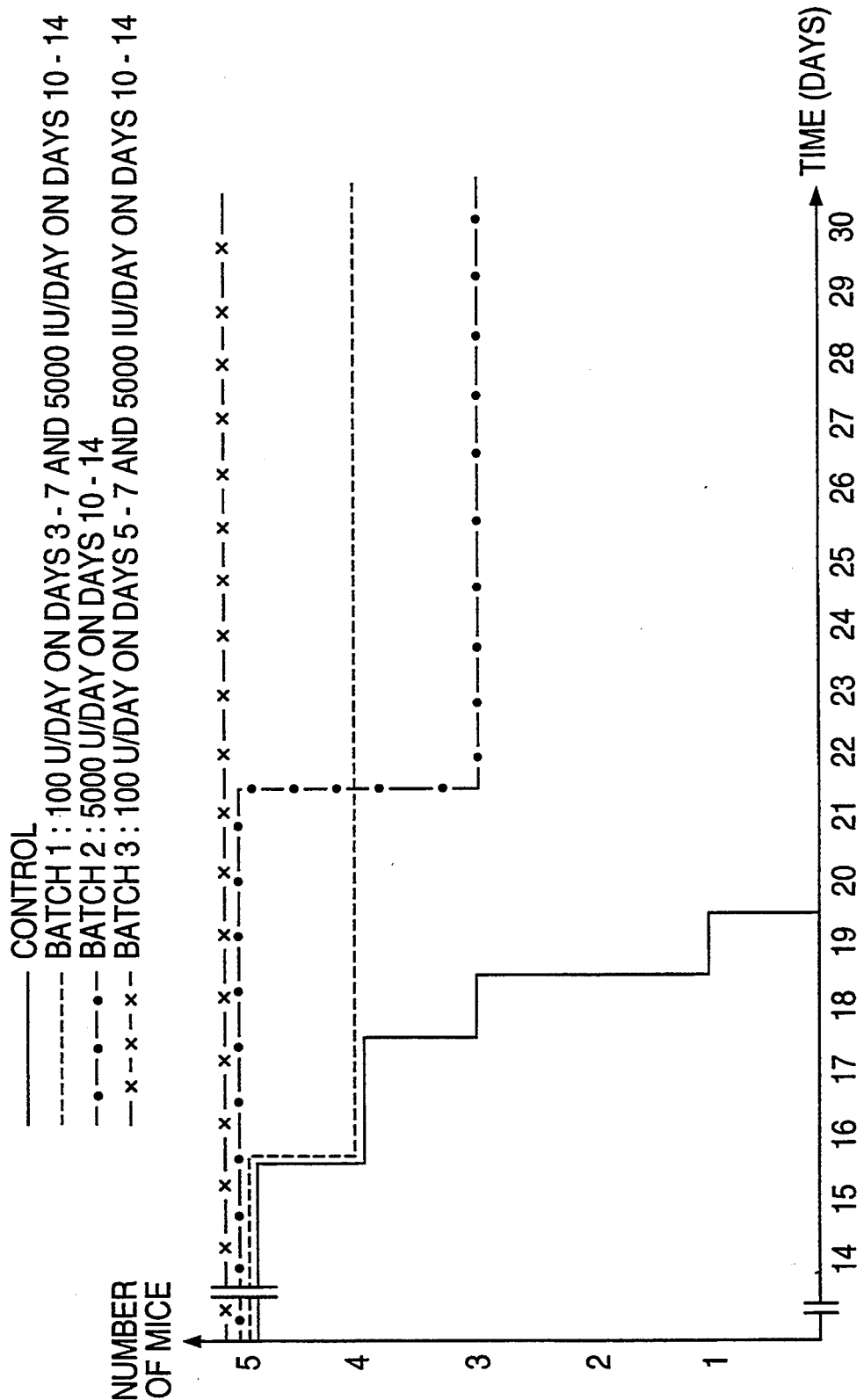

DRUGS CONTAINING A GLYCOSYLATED INTERLEUKIN-2

This application is a continuation of application Ser. No. 07/715,862, filed Jun. 17, 1991, which in turn is a continuation of Ser. No. 07/499,472, filed on Jun. 21, 1990, both now abandoned.

The invention relates to a novel glycosylated interleukin_2, a method of isolating it from the supernatant of a culture of recombined CHO cells secreting the protein, and a novel drug containing glycosylated interleukin_2.

Interleukin_2 (hereinafter sometimes called IL-2 for short) is a lymphokine secreted inter alia by the T lymphocytes of mammals in response to activation by an antigen or a mutogenic compound. It performs an essential function by acting on the proliferation and differentiation of various kinds of cells involved in immune responses (R. J. Robb (1984) Immunol. Today, 5, 203–209), and on other cells.

Glycosylated interleukin_2 of human, origin has been studied in more detail. It is known that it is produced in the form of a protein containing 133 amino acids and bearing an oligosaccharide structure fixed to the threonine radical in position 3 (H. S. Conradt et al (1986) Eur. J. Biochem., 153, 255–261). The T lymphocytes first synthesise it in the form of a precursor containing 153 amino acids and secrete it in the form of a protein containing 133 amino acids (called the mature glycosylated protein) after the 20 amino-acid signal peptide has been cut at the level of the endoplasmic reticulum, followed by glycosylation in the Golgi apparatus.

In view of the inadequate quantities of interleukin_2 obtained, either from peripheral lymphocytes or from a lymphoblastoid cell line such as the Jurkatt line, genetic recombination techniques appear promising, since they can be used to express the gene of a protein in a foreign host, in the case either of eucaryotic or procaryotic cells. Thus, the interleukin_2 gene has been successfully cloned and expressed in the *Escherichia coli* bacterium and in various eucaryotic cells, more particularly COS ape cells and CHO Chinese hamster ovary cells.

Recently the applicants have developed a method of preparing interleukin_2 from recombined CHO cells and resulting in high-level expression of the protein, which is obtained mainly in the form of glycosylated interleukin 2 (see application EP-A-307 285 and P. Ferrara et el (1987), Febs letters, 226, 1, 47–52). The applicants have therefore carried out research on isolating large quantities of glycosylated interleukin_2.

Separation and purification of a protein for pharmaceutical use, starting from a culture supernatant, are difficult problems. It is necessary to eliminate contaminating substances associated with the product fort system, inter alia proteins which contaminate the producing strain, nucleic acids, endotoxins, viruses potentially present and degraded forms of the isolated protein. Care must also be taken not to denature the protein, so as to preserve its activity and not provoke Interfering immune reactions in the patient. Furthermore, in the case of product ion on an industrial scale, the method of isolating the protein should preferably not use difficult techniques such as immunoaffinity and should guarantee good yields of isolated protein compared with the protein in the culture medium.

Processes for purifying natural and recombinant interleukin_2 have been described. K. Katok (Katok K (1985) Biochem and Biophys Commun, 127, 1, 182–190), for example, discloses a method of purifying interleukin_2 produced from a culture of activated peripheral lymphocytes and comprising the following steps in succession: cation exchange chromatography, an ion exchange chromatography, exclusion chromatography and reverse phase HPLC chromatography. M. P. Weir (Weir M. P. (1987) J. of Chromatography, 396, p. 209–215) describes a method of extracting and purifying recombinant interleukin_2 derived from *E. coli* and comprising the following steps: lysis of cells by sonication, extraction with butanol, dissolving of interleukin_2 aggregates in 8M guanidine chloride in the presence of dithiothreitol, exclusion chromatography, renaturation of the protein by dilution of guanidine chloride In the presence of copper sulphate, cation exchange chromatography and reverse-phase HPLC chromatography.

These methods involve a reverse-phase HPLC chromatography step, which can be used to obtain a high purification factor owing to the hydrophobic character of the molecule, but necessitate use of acid pH and organic solvents, which are harsh conditions capable of denaturing interleukin_2. They cannot purify the glycosylated interleukin_2 present In the culture supernatant of CHO cells in the manner which satisfies the aforementioned criteria.

The applicants were therefore surprised to find that it was possible, starting from the supernatant of recombined CHO cells, to isolate a novel glycosylated interleukin_2 having particularly interesting pharmaceutical properties, by a process which Is simple and usable on a large scale and comprises the following steps: separation of a fraction rich in interleukin_2 from the supernatant, cation exchange chromatography, hydrophobic interaction chromatography and exclusion chromatography. The invention therefore relates to a glycosylated interleukin_2 capable of being obtained from the supernatant of a culture of recombined CHO cells by a process comprising the following steps:

a) separation of a fraction rich in interleukin_2 from the culture supernatant,
b) cation exchange chromatography,
c) hydrophobic interaction chromatography and
d) exclusion chromatography.

This glycosylated interleukin_2 has a CTLL-2 activity greater than $15 \times 10^5$ U/mg, near the CTLL-2 activity of natural interleukin 2 (about $20 \times 10^5$ U/mg). After lyophilisation of glycosylated interleukin_2 solubilised in an aqueous solution at pH 6.5 and immediate reconstitution of the solute, the reconstituted solution is clear at a physiological pH and contains at least 80% of the initial CTLL-2 activity.

Preferably the recombined CHO cells are CHO dhfr- cells derived from the strain DXB11 by transformation by an expression vector for a precursor of interleukin_2 and DHFR. In this case, a preferred expression vector is a plasmid having the characteristics of plasmid pSV 726. The recombined CHO cells are preferably cultivated in a synthetic medium low in proteins. The medium may without disadvantage contain polyvinylpyrolidone, a compound which increases the specific output of interleukin_2 from the recombined CHO cells.

The invention also relates to a novel method of isolating glycosylated interleukin_2 from the supernatant of a culture of recombined CHO cells, characterised in that it comprises the following steps:
  a) separation of a fraction rich in interleukin_2 from the culture supernatant,
  b) cation exchange chromatography,
  c) hydrophobic interaction chromatography and
  d) exclusion chromatography.

The recombined CHO cells are cultivated on suitable media well known to the skilled addressee, preferably on synthetic media low in proteins, e.g. media containing about 4 mg/ml of total proteins. The media preferably contain polyvinylpyrrolidone.

Advantageously the fraction rich in interleukin_2 is separated from the culture supernatant by double filtration between a membrane 1 permeable to the protein and a membrane 2 which retains it. Membrane 1 is e.g. a microfiltration or ultrafiltration membrane. Membrane 2 is an ultrafiltration membrane. Preferably the membrane 1 has a stop threshold above 30 kDa, more particularly between 50 and 150 kDa, and membrane 2 has a stop threshold below 10 kDa, preferably between 5 and 10 kDa. Membranes 1 and 2 are advantageously made of cellulose acetate and polysulphone.

Advantageously the cation exchange step is carried out at a pH in the range between 4.5 and 6.5, more particularly between 5.2 and 5.7, on a chromatographic support comprising a rigid or semi-rigid gel based on hydrophilic polymers, such as agarose, cross-linked if required, or a polyacrylamide or a hydrophilic vinyl polymer, or silica coated with a hydrophilic polymer, groupings being grafted on to the support so as to give it strong cation-exchange properties. Sulphopropyls (SP) are preferred groupings of this kind.

The cation exchange chromatography step is preferably preceded by an anion exchange chromatography step.

In that case, the anion exchange step is preferably carried out at pH in a range between 5.5 and 8.5, more particularly between 6.5 and 8.2, on a chromatographic support comprising a rigid or semi-rigid gel based on hydrophilic polymers, such as a cross-linked agarose, or a polyacrylamide or a hydrophilic vinyl polymer, or silica coated with a hydrophilic polymer, groupings being grafted on to the support so as to give it weak anion exchange properties. Diethylaminoethyls (DEAE) are preferred groupings of this kind.

Advantageously the hydrophobic interaction step is carried out at a pH in the range between 4.5 and 8.0, more particularly between 6.0 and 8.0, on a chromatographic support for desorption of glycosylated IL-2 without addition of chaotrophic agents or organic solvents or aqueous solvents having a pH less than 4.5 or above 8.0. Examples of such supports are gels based an hydrophilic polymers such as a cross-linked agarose, or a hydrophilic vinyl polymer, or silica coated with a hydrophilic polymer. Butyl, phenyl or propyl groupings are grafted on to the supports.

Preferably the exclusion chromatography step is carried out at a pH in a range between 5.0 and 8.0, more particularly between 6.0 and 7.0, on a support having a fractionation range between 1 and 250 kDa. Advantageously the support is based on dextran cross-linked with acrylamide, or based on agarose.

The glycosylated interleukin_2 isolated by the aforementioned method, as compared with other purified recombinant interleukin_2, more particularly that derived from $E.$ $coli$, has properties very suitable for its use as the active principle of a drug, i.e. improved anti-tumour activity, excellent immunostimulating properties, greatly reduced toxicity, less immunogenicity, solubility in en aqueous solvent at a physiological pH without adding a toxic solubilising agent or chemically modifying the molecule, and excellent stability after lyophilisation in pharmaceuticaly acceptable formulations.

The invention therefore also relates to the drug in which the active principle is the glycosylated interleukin_2 as previously defined. The substance can be used alone or in association with other active principles such as other cytokins, e.g. interleukin_1, interleukin_4, $\alpha$-interferon, $\gamma$-interferon or TNF, or anti-turnout agents such as flavone acetate or cyclophosphamide or antimytotic agents or immunomodulators such as cyclosporin or BCQ, or antibodies or thymic hormones.

In all known or future applications of IL-2, and in associations of IL-2 with other active principles, the glycosylated IL-2 according to the invention will be an advantageous substitute for IL-2 derived from $E.$ $coli$.

These applications include the following:
Treatment of various conditions such as cancer, induced or acquired immunodeficiencies, immune anomalies (more particularly auto-immune and inflammatory diseases) and infectious diseases (inter alia microbial and parasitic viral infections);
Prophylactic treatment of the aforementioned conditions, more particularly of infectious diseases, and
Vaccination (using IL-2 as an adjuvant).

Glycosylated IL-2 and associations of glycosylated IL-2 with other active principles can be used in therapy by injection (intravenous bolus or in perfusion, subcutaneous, intramuscular, intraperitoneal or local, e.g. in tumours) into the ganglion or into other immunocompetent organs, or alternatively by action in vitro on cells selected from the patient or from donors.

The invention will be more easily understood from the following examples, given by way of illustration only.

BRIEF DESCRIPTION OF THE DRAWINGS

FIGS. 6–8 show the results of experiments performed in Example 9, to determine the in vivo activity of glycosylated interleukin 2 in stimulating the immune response to humoral mediation in BALB/C mouse, by measuring the primary splenic response to immunization with a thymo-dependent antigen, ovalbumin.

FIG. 9 shows the results of an experiment demonstrating the anti-tumor activity of glycosylated IL-2, as described in Example 10 and Table 5. The number of mice surviving during a 30-day period in batches 0 (control), 1, 2, and 3 are shown.

EXAMPLE 1

Construction of Vectors for Expressing a Precursor of Interleukin-2 and DHFR: Plasmids pSV 720 and pSV 726

The construction of plasmids comprises inter alia isolation of DNA fragments by using restriction enzymes starting from pre-existing vectors, chemical synthesis of oligonucleotides, fitting together the various fragments—after modifying their ends if required—by using an enzyme such as DNA ligase of bacteriophage T4, selection of plasmids after cloning (after bacterial transformation in *Escherichia coli*) and purification thereof.

The process uses techniques well known to the skilled addressee.

These techniques are described inter alia in the work entitled *Molecular Cloning: a Laboratory Manual* by T. Maniatis et al, published in 1982 by Cold Spring Harbor Press, New York (U.S.A.).

The set of restriction enzymes needed for constructing the vectors described hereinafter is sold inter alia by New England Biolabs (U.S.A.).

DNA ligase of bacteriophage T4 is available from New England Nuclear (U.S.A.).

a) Plasmid pSV 720

Figure 1:
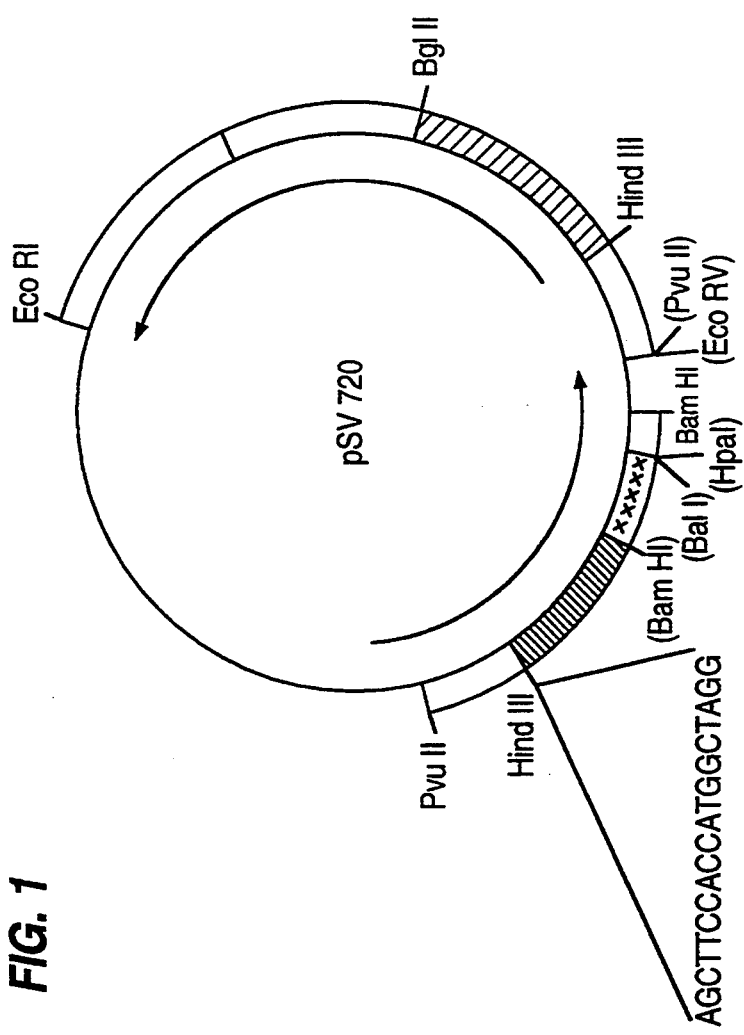
FIG. 1 shows plasmid construct pSV 720.

This substance, shown in FIG. 1, is a result of fitting together the following seven fragments of DNA by the previously-mentioned methods:

- A PvuII-HindIII fragment containing 342 base pairs (hereinafter called bp) obtained from genome SV 40 (W. Fiers (1978), Nature, 273, 113–120) and containing the early promotor of this virus:
- A HindIII-BamHI fragment of 504 bp containing a DNA sequence which codes for the natural precursor of IL-2 and in which the AGCTT-CCACAATGTACAGG nucleotide sequence situated at the 5' end of the coding strand is replaced by the synthetic sequence AGCTTCCAC-CATGGCTAGG, so as to obtain a sequence, at the level of the nucleotides surrounding the codon ATG, corresponding to the CCACCATGG consensus sequence described by M. Kozak ((1984) Nuc. Ac. Res., 12, 857–872)),
- A BamHI-BalI fragment of 305 bp, obtained from the gene of mouse alphaglobin (Y. Nishioka and P. Leder (1979) Cell, 18, 875–882) and containing the distal intron of this gene,
- An HpaI-BamHI fragment of 133 bp from the genome of virus SV 40 and containing the early polyadenylation signal of this virus,
- A BamHI-EcoRV fragment of 185 bp from plasmid pBR 322 (F. Bolivar (1977), Gene, 2, 95–113),
- A PvuII-EcoRI fragment of 2677 bp from plasmid pSV2-dhfr plasmid (S. Subramani et al (1981) Molecular and Cellular Biology, 1, 854–864) deposited in the ATCC collection, reference 37146 and
- An EcoRI-PvuII fragment of 2295 bp from plasmid pBR 322.

Plasmid pSV 720 contains:

A unit for expressing the natural precursor of IL-2. The promotor in this unit is the early promotor of virus SV 40; downstream of the coding sequence for the precursor of IL-2, the unit comprises a sequence containing the second intron of the gene of mouse alphaglobin followed by the early polyadenylation signal of virus SV 40, and A unit for expressing dhfr. The promotor in this unit is the early promotor of virus SV 40; downstream of the coding sequence for DHFR, the unit contains the sequence between the MboI sites in positions 4893 and 4083—using the W. Fiers notation—on the genome of virus SV 40 and containing an intron for the t antigen of the virus SV 40 followed by the early polyadenylation signal of the virus SV 40. This unit is contained in the PvuII-EcoRI fragment from plasmid pSV2-dhfr.

b) Plasmid pSV 726

Figure 2:
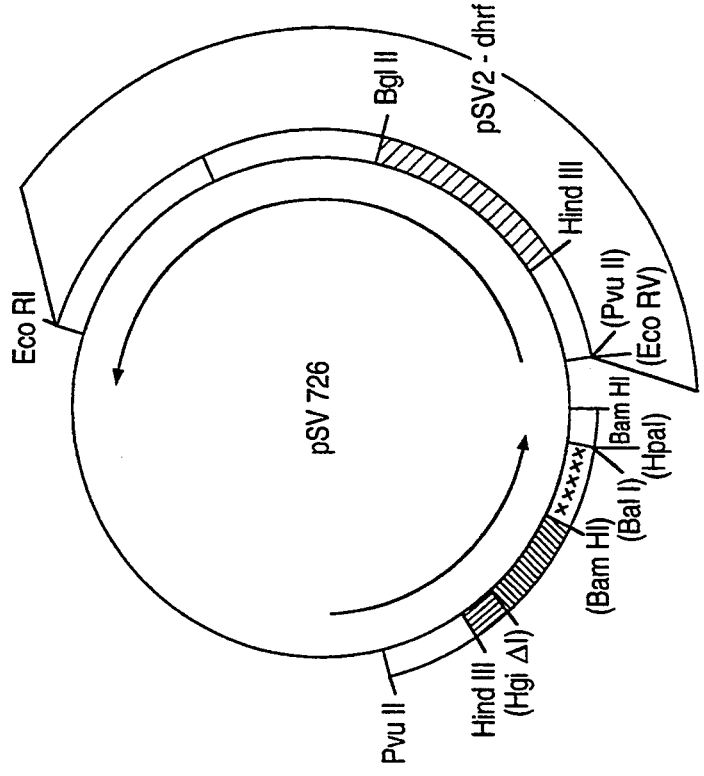
FIG. 2 shows plasmid construct pSV 726.

This plasmid, shown in FIG. 2, is obtained from plasmid pSV 720 as follows:

The DNA segment between the HindIII and HgiAI restriction sites situated in the upstream part of the HindIII-BamHI segment of plasmid pSV 720 and containing the sequence corresponding to the modified signal peptide (it contains an alanine radical in the 2 position instead of the tyrosine radical owing to adoption of a sequence corresponding to the Kozak consensus sequence) of the natural precursor of IL-2 and of the first amino acid of mature IL-2, is then replaced by a synthetic double-strand oligonucleotide which from its ninth nucleotide codes for the signal peptide of the natural precursor of the human growth hormone hGH, (hereinafter called hGH signal peptide) and for the first amino acid of mature IL-2.

The resulting plasmid is plasmid pSV 726, in which the HindIII-BamHI segment carries the coding sequence for a precursor of IL-2 (the precursor ps-hGH-IL-2) comprising the signal peptide of hGH.

The plasmid pSV 726 contains:

A unit for expressing the precursor (ps-hGH)-IL-2. The promotor in this unit is the early promotor of virus SV 40; downstream of the coding sequence for the precursor of (ps-hGH)-IL-2, the unit comprises a sequence which contains the second intron of the the gene of mouse alphaglobin followed by the early polyadenylation signal of virus SV 40, and A unit for expressing dhfr. The promotor in this unit is the early promotor of virus SV 40; downstream of the coding sequence for dhfr, the unit comprises the sequence between the MboI sites in positions 4683 and 4083—using the W. Fiers notation—on the genome of virus SV 40 and containing an intron for the t antigen of virus SV 40 followed by the early polyadenylation signal of virus SV 40. This unit is contained in the PvuII-EcoRI fragment from plasmid pSV2-dhfr.

EXAMPLE 2

Preparation of Cell Lines Giving a High Yield of Interleukin-2, i.e. Lines 58-12 and 109-27

CHO dhfr− cells of the DXB11 strain (a clone of CHOK$_1$ DHFR-described by URLAUB et al in PNAS U.S.A. (1980) 77, 7, page 4218–4220) were transfected with plasmid pSV 728 or plasmid pSV 720.

The method of operation was that described by F. Graham and A. Van der Eb, ((1973) VIrology, 54, 538–539).

The cells were first propagated in alpha-MEM (Gibco) medium mixed with 10% (v/v) of foetal calf serum, 20 μg/ml of gentamycin, 60 μg/ml of tylocin and 300 μg/ml of L-glutamine (this medium is hereinafter called non-selective medium).

After a washing phase, the cells seeded the previous day were covered with non-selective medium and 10 μg of one of the plasmids was added in the presence of calcium phosphate but without salmon sperm DNA. Cells prepared in this manner were incubated at 37° C. for 7 hours.

The cells were then cultivated at 37° C. for 3 days in alpha-MEM medium also containing 5% (v/v) of foetal calf serum. At the end of incubation, the cells were divided in portions of $5.10^5$ per Petri dish in minimum essential medium sold by Messrs Gibco, reference 041-1095. In the present case the medium was used mixed with dialysed Gibco foetal calf serum (10% v/v), gentamycin (20 μg/ml), tylocin (50 μg/ml), L-glutamine (300 μg/ml) and L-proline (150 μg/ml). The medium containing these additions is hereinafter called selective medium.

The thus-prepared cells were incubated at 37° C. for 2 weeks, the selective medium being renewed every 3 days. The colonies observed at the end of the incubation had all come from cells which had effectively incorporated a plasmid. These colonies were taken and separately recultivated in selective medium and tested by measuring the IL-2 type activity to ascertain their suitability for producing IL-2.

This IL-2 type activity is the biological activity of the culture medium in the test of stimulation of the proliferation of the CTLL-2 dependent IL-2 mouse lymphocyte T line (P. Baker et al, J. Exp. Med., 1979, 149–173). This activity will hereinafter be called CTLL-2 activity and expressed in units (hereinafter abbreviated to U) with respect to the standard defined in the B R M P (Biological Res. Modifiers Program (1984), Lymphokin Res. 4, 193–227).

The most productive colonies were successively subcultured in four preparations of selective medium, each preparation having a greater concentration (0.02, 0.05, 0.1 and 0.2 uM) of methotrexate (amethopterin, Sigma) than the preceding preparation, in the manner described by F. Alt et al (1978 Journal of Biological Chemistry, 253, 1357–1570).

The substances thus retained were the CHO 58.12 line transformed by plasmid pSV 720 and the 109.27 line transformed by plasmid pSV 726, both lines being highly productive of interleukin 2.

EXAMPLE 3

Cultivation of Lines Highly Productive of Interleukin_2, i.e. the CHO 58-12 and 109-27 Cell Lines I. Production of IL-2 from the CHO 58-12 Line in a Culture Medium Moderately Rich in Proteins After a sufficient number of cells had been obtained by propagation in Rollers boxes (rotary flasks) a production fermenter was inoculated with about 300,000 cells/ml. The fermentation conditions were as follows:

a) Cultivation with perfusion at a perfusion rate of 1 volume per day approximately;

b) The supernatant was continuously collected after travelling through a spin filler (rotating filler secured to the agitator shaft);

c) Cultivation on microspheres of cross-linked dextran covered by a film of denatured collagen (Cytodex III R, sold by Messrs PHARMACIA);

d) pH of culture adjusted to about 7.3;

e) Dissolved oxygen pressure adjusted to 30% (100% being defined as saturation of the medium with oxygen after bubbling of air);

f) The temperature of the culture was adjusted to about 37° C.;

g) The basic culture medium, called medium 1, was mainly based on the following mixture (50:50): Eagle MEM (FLOW) minimum essential medium and F12 Ham (GIBCO) nutrient medium.

The composition of medium 1 is given hereinafter:

| AMINO ACIDS | MW | mg/l | mM |
|---|---|---|---|
| L- Alanine | 89.09 | 13.35 | 0.15 |
| L- Arginine. HCl | 210.7 | 168.5 | 0.8 |
| L- Asparagine. H$_2$O | 150 | 22.5 | 0.15 |
| L- Cysteine. 2HCl | 313.2 | 15.65 | 0.05 |
| L- Cysteine. HCl. H$_2$O | 175.6 | 17.55 | 0.10 |
| L- Glutamic acid | 147 | 22.05 | 0.15 |
| L- Glutamine | 146 | 292 | 2 |
| L- Glycine | 75.07 | 11.25 | 0.15 |
| L- Histidine. HCl.H$_2$O | 209.7 | 31.48 | 0.15 |
| L- Isoleucine | 131.2 | 27.97 | 0.21 |
| L- Leucine | 131.2 | 32.55 | 0.25 |
| L- Lysine. HCl | 182.7 | 54.5 | 0.30 |
| L- Methionine | 149.2 | 9.74 | 0.065 |
| L- Phenylalanine | 165.2 | 18.5 | 0.11 |
| L- Proline | 115 | 28.75 | 0.25 |
| L- Serine | 105 | 15.75 | 0.15 |
| L- Threonine | 119.1 | 30 | 0.25 |
| L- Tyrosine | 181.2 | 29.89 | 0.165 |
| L- Tryptophan | 204.2 | 6 | 0.03 |
| L- Valine | 117.2 | 28.85 | 0.246 |
| L- Aspartic acid | 133 | 19.95 | 0.15 |

| INORGANIC SALTS | MW | mg/l | mM |
|---|---|---|---|
| CaCl$_2$ | 110.99 | 86.5 | 0.78 |
| KCl | 74.56 | 311.8 | 4.18 |
| KH$_2$ PO$_4$ | 136.09 | 30 | 0.22 |
| FeSO$_4$.7H$_2$O | 278.02 | 1.8 | $6.5\ 10^{-3}$ |
| MgSO$_4$ | 120.37 | 48.84 | 0.4 |
| NaCl | 58.44 | 7800 | 133 |
| NaHCO$_3$ | 84.01 | 350 | 4.1 |
| MgCl$_2$ | 95.22 | 28.5 | 0.3 |
| Na$_2$HPO$_4$ | 141.96 | 94.94 | 0.67 |

| OLIGO-ELEMENTS | MW | mg/l | mM |
|---|---|---|---|
| CuSO$_4$.5H$_2$O | 249.68 | $1.5\ 10^{-3}$ | $6\ 10^{-6}$ |
| MnSO$_4$.H$_2$O | 169.02 | $0.845\ 10^{-3}$ | $5\ 10^{-6}$ |
| Na$_2$SeO$_3$.5H$_2$O | 263.01 | $3.42\ 10^{-2}$ | $1.4\ 10^{-4}$ |
| NiCl$_2$.6H$_2$O | 237.70 | $1.19\ 10^{-6}$ | $5\ 10^{-9}$ |
| (NH$_4$)$_6$ Mo$_7$O$_{24}$.4H$_2$O | 1235.89 | $1.235\ 10^{-3}$ | $1\ 10^{-6}$ |
| NH$_4$ VO$_3$ | 116.99 | $5.845\ 10^{-4}$ | $5\ 10^{-6}$ |
| SiO$_2$ Na$_2$O.5H$_2$O | 212.14 | 0.1067 | $5\ 10^{-4}$ |
| SnCl$_2$.2H$_2$O | 225.63 | $1.12\ 10^{-6}$ | $5\ 10^{-9}$ |
| Zn SO$_4$.7H$_2$O | 287.54 | 2.13 | $7\ 10^{-3}$ |

| VITAMINS | MW | mg/l | mM |
|---|---|---|---|
| Biotin | 244.3 | $3.65\ 10^{-3}$ | $0.015\ 10^{-3}$ |
| Choline chloride | 139.6 | 7.48 | 0.05 |
| Folic acid | 441.4 | 2.45 | 0.003 |
| Nicotinamide | 122.13 | 0.513 | $4.6\ 10^{-3}$ |
| Pyridoxal. HCl | 203.63 | 0.5 | $2.5\ 10^{-3}$ |
| Pyridoxine. HCl | 205.6 | 0.031 | $3\ 10^{-4}$ |
| Riboflavin | 376.4 | 0.069 | $2\ 10^{-4}$ |
| Thiamine. HCl | 337.3 | 0.67 | $2\ 10^{-3}$ |
| Cyanocobalamine | 1355.4 | 0.68 | $5\ 10^{-4}$ |
| Calcium D pentothenate | 238.3 | 0.74 | $3\ 10^{-3}$ |

| OTHER CONSTITUENTS | MW | mg/l | mM |
|---|---|---|---|
| Glucose | 18 | 1800 | 10 |
| Phenol red (sodium salt) | | 11 | |
| Sodium pyruvate | 110 | 110 | 1 |
| Hypoxanthine (sodium salt) | 136.1 | 2.38 | $1.75\ 10^{-2}$ |
| Lipoic acid | 206.3 | 0.105 | $5\ 10^{-4}$ |
| Linoleic acid | 278.44 | 0.042 | $1.5\ 10^{-4}$ |
| Putrescine 2HCl | 161.1 | 0.0805 | $5\ 10^{-4}$ |
| i-Inositol | 180.2 | 10 | $5.5\ 10^{-2}$ |
| Thymidine | 242.2 | 0.365 | $1.5\ 10^{-3}$ |
| MOPS | 209.3 | 6279 | 30 |

The fermentation process was in two parts, called the growth phase and the production phase. During the growth phase, foetal calf serum (5%) was added to the medium. During the production phase, the medium was mixed with a protein fraction called F IV-1, isolated from bovine serum by the Cohn fractionation method. The culture medium was moderately rich in proteins (400 mg of total proteins/l). Production was continued for at least 30 days. The harvest was cooled in line at a temperature of +6° C. The concentration of total proteins was 500 mg/l. The CTLL-2 activity in the culture supernatant was 40,000 U/ml, i.e. an IL-2 concentration of about 2 mg/l (assuming the IL-2 specific activity to be $2\times10^7$ U/mg and the IL-2 protein purity to be 0.4%). This culture supernatant will hereinafter be called culture supernatant A.

II. Production of IL-2 from the CHO 109-27 Line in a Medium Low in Proteins

After a sufficient number of cells had been obtained by propagation in Rollers boxes (rotating flasks), a production fermenter was inoculated therefrom with 300,000 cells/ml approx. The fermentation conditions were as follows:
a) Cultivation with perfusion at a perfusion rate of about 1 volume per day;
b) The supernatant was continuously collected after travelling through a spin-filter;
c) Growth on microspheres of cross-linked dextran covered with a film of denatured collagen (Cytodex III R, said by Messrs PHARMACIA);
d) pH of culture adjusted to about 7.3;
e) Dissolved oxygen pressure adjusted to 100%;
f) Temperature of culture adjusted to about 37° C., and
g) The basic culture medium was the medium 1 defined hereinbefore.

The fermentation process was in two parts, called the growth phase and the production phase. During the growth phase the medium was mixed with foetal calf serum (2.5%). During the production phase, the serum was replaced by 3 mg/l of insulin and 1 mg/l of lactoferrin, the only proteins in the medium.

During this phase, 0.5% of polyvinylpyrrolidone having an average molecular weight of 40,000 was also added to the medium. It has been found that this polymer can increase the specific output of IL-2 from recombined CHO cells (the quantity of IL-2 secreted per unit time and unit biomass). Accordingly, the culture medium was a synthetic medium low in proteins (4 mg/l of total proteins). Production was kept up for at least 30 days. The harvest was cooled in line at a temperature of +6° C. The concentration of total proteins in the culture supernatant was 100 mg/l. The CTLL-2 activity was 120,000 U/ml, i.e. a concentration of about 6 mg/l and a protein purity of 6%. The culture supernatant will hereinafter be called culture supernatant B.

EXAMPLE 4

Partial Characterisation of IL-2 Secreted by the CHO 58-12 and 109-27 Cell Lines 1. Purification of IL-2

IL-2 was purified from a liter of culture supernatant.
The first step was concentration and a first purification by subjecting the supernatant to ion exchange chromatography on a SepharoseR agarose column (S-Fast Flow—Pharmacia Fine Chemical—Sweden), which had previously been balanced with 0.05M ammonium acetate at pH 4.5. Elution was carried out with 0.05M ammonium acetate (pH 5.5) also containing NaCl (molarity 0.05M, then 0.5M).

The eluted fragments, which were shown to be biologically active by measuring their CTLL-2 activity, were collected and their pool was subjected to high-performance liquid chromatography on a reverse-phase column. The chosen support was a C3 grafted silica gel. The column dimensions were 1.0×25.0 cm.

Elution was carried out at a linear acetonitrile gradient varying from 5 to 100%, (v/v) in an 0.1% aqueous solution (v/v) of trifluoroacetic acid, In 80 minutes and at a flow rate of 4 ml/min.

The biologically active eluted fractions were collected and their pool was subjected to chromatography of the same kind as before but inter alia under identical elution conditions, on C18 grafted silica gel in a column measuring 2.1×10.0 cm.

The pool of biologically active eluted fragments collected during the chromatography had more than 95% IL-2 purity, as shown by electrophoresis on polyacrylamide gel in the presence of sodium dodecyl sulphate (Laemli, (1970) Nature, 277, 680–685). This pool was the material used for characterising IL-2.

2. Characterisation of IL-2 by Determining the Terminal Amino Sequence

The samples for treatment were brought to the surface of a hexadimethrine bromide (or polybrene) filter. The filter was inserted into a protein sequencer (model 470 A sold by Applied Biosystems (U.S.A.)) equipped with a chromatograph (Applied Biosysystems Model 430 A) which continuously analysed the phenylthiohydantoic derivatives formed, after each degradation cycle.

The results of this determination agree with the sequence already published for the natural product (R. Robb et al (1984) Proc. Natl. Acad. Sci. U.S.A., 81, 6486–6490), except as regards position 3, where no amino acid was detected. This non-detection is explained by the presence of an oligosaccharide in position 3.

The sequence is written as follows, In the case of the first ten amino acids:

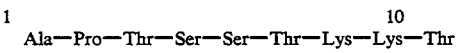

Alanine is the only radical detected at the terminal N position. This confirms that, the precursor (ps-hGH)-IL-2 was properly cut during secretion.

EXAMPLE 5

Isolation of Glycosylated Interleukin_2 by the Method According to the Invention, Starting from the Culture Supernatant of the CHO 109-27 Line In this example and in Example 7, the water used was demineralised water purified in a Milli-Q type apparatus and ultrafiltered.

1. Separation of the Culture Medium from a Fraction Rich in Interleukin-2

130 liters of the supernatant of medium B described in Example 3 were taken and pre-filtered on an 8 μm stop threshold filter so as to eliminate large particles capable of clogging the ultrafiltration membranes.

The interleukin_2, the molecular weight of which was between 15 kDa and 17 kDa, was fractionated and then concentrated by double tangential ultrafiltration between a first membrane having a stop threshold of 100 kDa and a second membrane having a stop threshold of 10 kDa, operating in the manner described hereinafter. The first and the second membrane were spiral cartridges of cellulose acetate, i.e. membranes YM 100 and YM 10 said by Messrs AMICON, mounted in cascade so that the filtrate from the first membrane supplied the material retained by the second membrane.

The prefiltrate was fed to the first membrane and, to begin with, the material retained by the first membrane and by the second membrane was concentrated until the volume of material retained by the first membrane was about 15 liters. Next, the retained material was diafiltered (washed at constant volume) with 80 liters of ultrapurified water so as to remove all the IL-2 from the material retained by the first membrane and reduce the ionic force of the material retained by the second membrane. Next, the latter material was concentrated to 1.5 liters and the interleukin_2 was recovered after rinsing the membrane with water. The resulting concentrate was filtered through a filter having an 0.2 μm stop threshold, so as to eliminate certain precipitates formed during ultrafiltration. The product was 2.4 liters of concentrated aqueous solution of IL-2.

2. Isolation of Glycosylated Interleukin_2 a) Anion Exchange Chromatography

In this step, some of the contaminants such as nucleic acids, endotoxins and CHO proteins and other proteins present in the supernatant culture, were eliminated by fixing on a chromatographic support. The IL-2 was not retained in the column under the chosen elution conditions. The chromatographic support used was a gel based on weak anion-exchange cross-linked agarose, i.e. DEAE Sepharose fast flow sold by Messrs PHARMACIA, placed in a glass column 140 mm in diameter at a height of 210 mm. Crystals of ammonium acetate were added to the previously-obtained concentrated IL-2 solution so as to adjust its conductivity to 5 mS/cm, and an ammonium acetate buffer solution, pH 7, was injected into the previously-balanced chromatographic support. Next, the column was washed with the last-mentioned solution. The fixation effluent and the washing solution containing IL-2 were combined. The product was 7.08 liters of aqueous solution rich in IL-2.

b) Cation Exchange Chromatography

This step was for removing some of the contaminants, such as polyvinylpyrrolidone, CHO proteins and other proteins present in the culture supernatant and not fixed on the anion chromatographic support, and for separating the different forms of IL-2.

The chromatographic support used was a gel based on hydrophilic polyvinyl resin, SP Fractogel 650 (S) sold by Messrs MERCK, placed in a column 50 cm in diameter at a height of 230 min. The pH of the solution obtained in the previous step was adjusted to 5.5 by adding acetic acid, and the solution was injected into the column. Next, the IL-2 fixed on the column was eluted by a solution having an increasing ionic force and obtained by mixing an aqueous solution of ammonium acetate (50 mM at pH 5.5) in various proportions with a 2M aqueous solution of sodium chloride. The optical density of the solution was measured at 280 nm. In this manner, the following three fractions containing the protein were separated:

Fraction 1, containing disialilated glycosylated IL-2 (form $N_2$)[1]

Fraction 2, containing monosialilated glycosylated IL-2 (form $N_1$)[1], and

Fraction 3, containing non-sialilated glycosylated IL-2 (form $N_0$)[1] and non-glycosylated IL-2 (form M)[1].

(1) cf. H. Conradt (1985T, Eur. J. Biochem. 153, 255–261 for a description of the various forms of IL-2.

Fractions 1 and 2 were combined, to obtain 0.45 liters of aqueous solution of glycosylated IL-2.

c) Hydrophobic Interaction Chromatography

The chromatographic support used was a hydrophobic interaction gel based on hydrophilic polyvinyl resin, i.e. Butyl Fractogel 650 (M) said by Messrs MERCK, and placed in a column 70 mm in diameter at a height of 135 min.

Ammonium sulphate up to molarity of 1.2M and ammonia for adjusting the pH to 6.5 were added to the previously-obtained solution of glycosylated IL-2, which was injected into the chromatographic support, which had previously been balanced with an aqueous solution (pH 6.5 and molarity 50 mM of ammonium phosphate and 1.2M of ammonium sulphate). In these conditions the glycosylated IL-2 was retained on the chromatographic support. The products not retained were eliminated by washing with the aforementioned solution followed by an aqueous solution (pH 6.5 and molarity 50 mM of ammonium phosphate and 0.8M ammonium sulphate). Next, the IL-2 was eluted with an aqueous solution (pH 3.5, 50 mM) of ammonium phosphate and 0.1M ammonium sulphate. The product was 2.17 liters of aqueous solution of glycosylated IL-2.

d) Exclusion Chromatography

The exclusion chromatography support was a gel based on cross-linked dextran and having a fractionation range between 250 and 5 kDa, i.e. Sephacryl S 200 HR said by Messrs PHARMACIA, placed in a column 100 mm in diameter at a height of 900 min.

After the solution obtained at the end of step c) had been concentrated on a cellulose acetate spiral membrane having a stop threshold of 10 kDa, the solution was injected into the column, which had previously been balanced with a 50 mM aqueous solution of sodium phosphate at pH 6.5, the glycosylated IL-2 was then eluted with the last-mentioned solution. The solution was detected at the column outlet by measuring the optical density at 280 nm. The various fractions collected were combined in accordance with their purity, analysed by reverse phase HPLC.

The product was 0.60 liters of a solution of glycosylated IL-2 in sodium phosphate.

3. Checking the Purity of the Product

Electrophoresis on Polyacrylamide Gel in the Presence of SDS

Electrophoresis on PAGE-SDS polyacrylamide gel (sodium dodecyl sulphate) in the presence of a reducer (dithiothreitol) was carried out by the method of LAEMMLI (U. K. LAEMMLI, Anal. Biochem (1977), 78, page 459) and followed by dyeing with silver by the method of MERRIL (C. R. MERRIL., Proc. Nat. Acad. Sci. U.S.A., 1979, vol. 76, page 4335).

Figure 3:
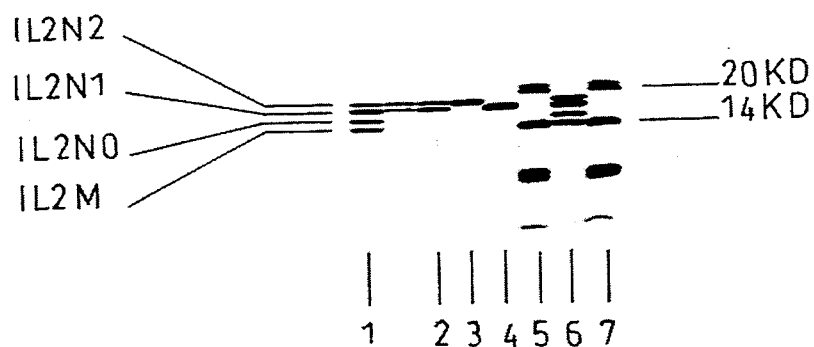
FIG. 3 shows a PAGE-SDS electrophoretogram of glycosylated IL-2 isolated according to Example 5.

The resulting electrophoregram, shown in FIG. 3, confirms that the purity of the glycosylated IL-2 was greater then 99.5%.

Analysis by HPLC on Reverse Phase Column

The chromatographic support was a grafted silica gel, i.e. Nucleosil C4 300 A, particle size 5 μm, sold by Société Francaise de Chrometo-colonne. Elution was carried out with a 6-minute gradient from (70% A+30%, B) to (25% A+75% B). A denotes an aqueous solution containing 0.1% trifluoroacetic acid and B denotes a solution of acetonitrile containing 0.1% of trifluoroacetic acid.

Figure 4:
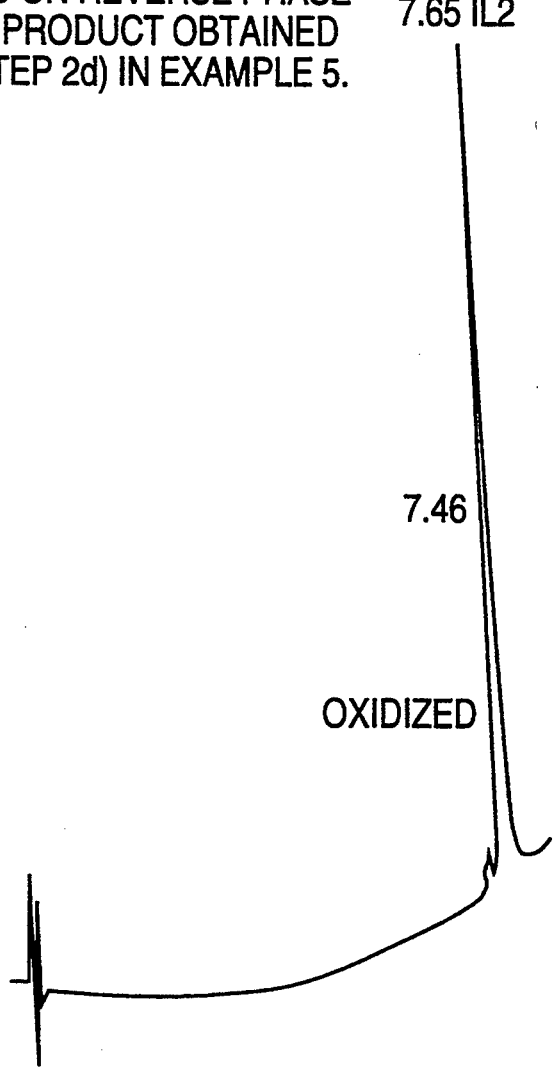
FIG. 4 shows a reverse phase HPLC analysis of the product obtained at the end of step (2d) in Example 5.

The resulting chromatogram, shown in FIG. 4, indicates a single impurity making about 5.5% of the total product. The impurity was partially characterised—it was oxidized glycosylated IL-2, which also had CTLL-2 activity.

Analysis by HPLC on Cation Exchange Column

The chromatographic support was a silica gel coated with a poly-aspartic acid, "polycat A 5 μm 300 A" said by Messrs CLUZEAU. Elution was carried out at a gradient of 3.5 mm from (85% A′+15% B′) to (75% A′+25% B′) and of 6.5 mm from (75% A′+25% B′) to (50% A′+50% B′), A′ denoting a solution of $KH_2PO_4$ (pH 5.0, molarity 25 mM) and B′ denoting a solution of $KH_2PO_4$ (pH 5.0, molarity 25 mM) and 1M sodium chloride.

Figure 5:
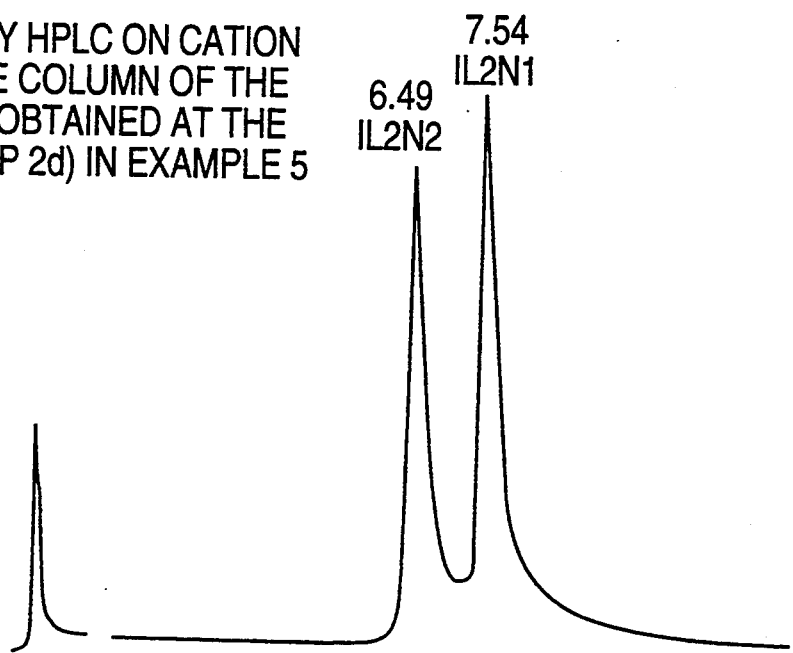
FIG. 5 shows an analysis by HPLC using cation exchange of the product obtained at the end of step (2d) in Example 5.

The resulting chromatogram, shown in FIG. 5, can be used to quantify the two forms of glycosylated IL-2 present, i.e. 48% of IL-2(N2) and 52% of IL-2(N1). In other experiments, the N2 predominates.

4. Balance

At the end of each of the isolation steps, the quantity of IL-2 present in the retained product was measured by metering the CTLL-2 activity thereof. The various forms of IL-2 had the same CTLL-2 activity.

The results are given in Table 1 hereinafter.

TABLE I

| Product retained at end of the step | Volume (l) | Total CTLL-2 activity ($10^{10}$ U) | CTLL-2 activity per unit volume (U/ml) | Yield |
|---|---|---|---|---|
| Production (supernatant | 127 | 1.521 | $1.2 \times 10^{-5}$ | |
| 1- | 2.4 | 1.290 | $4.8 \times 10^{-6}$ | 85% |
| 2- a) | 7.08 | 1.212 | $1.2 \times 10^{-6}$ | 94% |
| 2- b) | 0.45 | 0.982 | $2.2 \times 10^{-7}$ | 81% |
| 2- c) | 2.17 | 0.874 | $3.6 \times 10^{-6}$ | 89% |
| 2- d) | 0.60 | 0.751 | $1.2 \times 10^{-7}$ | 86% |

Total yield = 49.4%

As the Table shows, the CTLL-2 activity per unit, volume is 100 times more concentrated at the end of step 2-d) than in the culture supernatant, and the total yield of glycosylated IL-2 is about 50% relative to the total IL-2 present in the supernatant.

EXAMPLE 6

Characterisation of Glycosylated Interleukin 2 Isolated by the Method According to the Invention, Starting from the Culture Supernatant of the CHO 109.27 Cell Line Determination of specific CTLL-2 Activity = $(18 \pm 3) \times 10^5$ U/mg Determination of the Terminal Amino Sequence.

Samples of product were brought to the surface of a hexadimethrine bromide (or polybrene) filter. The filter was inserted into a protein sequencer (model 470 A, sold by Applied Biosystems (USA)) equipped with a chromatograph (model 430 A—Applied Biosystems) which continuously analysed the phenyl thiohydantoic derivatives formed.

The results of this determination agree with the already-published sequence for the natural product (R. Robb et al (1984) Proc. Natl. Acad. Sci. U.S.A., 81, 6486–6490) except as regards position 3, where no amino acid was detected. This non-detection is explained by the presence of an oligosaccharide in position 3.

The first six amino acids of this sequence are as follows:

1                                          10
Ala—Pro—Thr—Ser—Ser—Ser—Thr—Lys—Lys—Thr

Determination of the Primary Structure

The product, reduced and carboxymethylated, was digested overnight at ambient temperature by the action of trypsin added in a proportion of 1/30 (weight/weight) and the peptides obtained were separated by reverse phase HPLC chromatography by means of an acetonitrile gradient (in the presence of 0.1% trifluoroacetic acid) by the method published in Journal of IKmmunological Methods (1985), 81, 15–30.

Each purified tryptic peptide was subjected to analysis of amino acids and some were subjected to an Edman degradation.

It was thus possible to analyse the complete sequence of amino acids in the isolated product. This corresponds to that already published for the natural product (R. Robb et al (1984) Proc. Natl. Acad. Sci. U.S.A., 81, 6486–6490).

A study of the tryptic peptide maps of the product obtained after reaction with vinyl-4-pyridine, before and after reduction of the product with dithiothreitol, shows a disulphide bridge between cystein 58 and cystein 105 and a free thiol group (SH) for cystein 125.

Analysis of the Oligosaccharides

Electrophoresis on polyacrylamide gel in the presence of SDS revealed two forms of the product, having molecular weights of about 16.5 and 16.0 kDa corresponding to forms $N_1$ and $N_2$ (see FIG. 3). Treatment with neuraminidase (P. Ferrara et al (1987), 226, 1, 47–52) resulted in disappearance of the two observed bands and the appearance of a band having a molecular weight of 15.5 kDa and corresponding to form No (see FIG. 3), indicating that the differences between the two are due to the presence of sialic acids in the molecule. The product was analysed by chromatoelectrofocalisation, thus confirming this result and determining the isoelectric points of these two constituents, i.e. 7.0 for the form having a molecular weight of 16.5 kDa and 7.6 for the form having a molecular weight of 16 kDa.

Characterisation of the Structure of the Sugars

The sugars were further analysed by treatment of the substance corresponding to the 15.5 kDa band (obtained by treatment with neuramidinase) with a specific o-glucanase (i.e. the o-glucanase sold by GENZYME, reference 20 0-ASE). This enzyme treatment reduced the molecular weight of the substance from 15.5 to 15.0 kDa without changing the charge of the substance. Finally the purified terminal N tryptic peptides of Form $N_1$ and Form $N_2$ were analysed by FAB MS (Fast Atom Bombardment Mass Spectrometry). The results confirmed the presence of N-acetylgalactosamine, galactose and two neuraminic acids on the terminal N tryptic peptide of form $N_2$ and the presence of N-acetylgalactosamine, galactose and one neuraminic acid on the terminal N tryptic peptide of form $N_1$. The structure of the sugars for forms $N_1$ and $N_2$ of glycosylated IL-2 according to the invention was identical with the structure of the sugars of forms $N_1$ and $N_2$ described by Conradt et al (1985), Eur. J. of Biochemistry, 153, 255–261).

Immunological Properties of Glycosylated IL-2

There is a relation between the conformation of a protein and its antigenic properties, which can therefore be studied to give information about the three-dimensional structure of the molecule.

The antigenic properties of glycosylated IL-2 ($N_1+N_2$) and of natural IL-2 (BIOTEST-RFA) and IL-2 coli prepared as described in Example 8) were studied and compared, using two RIA (Radio-Immuno-Assay) systems. In the first (RIA A), use was made of a natural anti IL-2 monoclonal antibody (antibody BG5 supplied by the Centre Régional de Transfusion Sanguine de Besancon). In the second (RIA B), use was made of an anti IL-2 coil sheep antiserum (batch No. Pol-1/00-09 of CELLTECH UK.). In both cases the tracer was IL-2 (N2) tagged with iodine 125.

Table 2 hereinafter gives the $IC_{50}$ values (i.e. the concentration of IL-2 capable of displacing 50% of the tagged IL-2 (N2) of the antibody under consideration) obtained from the displacement curves for each of these systems (the values and typical deviations shown were calculated from three independent measurements of this parameter).

TABLE 2

| $IC_{50}$ with system RIA A (pM) | $IC_{50}$ with system RIA B (pM) |
|---|---|
| Glycosylated IL-2 ($N_1 \pm N_2$) 57 ± 9 | 124 ± 18 |
| IL-2 coli 135 ± 6 | 204 ± 18 |
| Natural IL-2 (BIOTEST-RFA) 58 ± 6 | 118 ± 18 |

It appears that the IC50 values obtained for glycosylated IL-2 ($N_1+N_2$) and for natural IL-2 are similar whereas they are significantly different from the values observed for IL-2 coli, a result which is particularly clear and reliable with the system RIA A, where the antibody is monoclonal. This finding shows a resemblance in three-dimensional structure between glycosylated IL-2 (N1+N2) and natural IL-2, and a difference in three-dimensional structure between glycosylated IL-2 (N1+N2) and IL-2 coli, which therefore have different antigenic determinants. Now, one of the problems with IL-2 coli is its immunogenicity (Krigel R. L. et al (1988) Cancer, Res. 48, 3875–3881 and Allegretta M. et al. (1988) J. of Clin. Immun. 6, 6, 481–490). It is very probable that these problems are due to epitopes specific to IL-2 coli and absent from natural IL-2. It is very likely, and confirmed by the aforementioned results, that glycosylated IL-2, which resembles natural IL-2 in structure and method of synthesis, does not have these epitopes.

EXAMPLE 7

Isolation of Glycosylated Interleukin_2 by the Method According to the Invention, Starting from the Supernatant Culture of the 58.12 Cell Line 1. Separation of a Fraction Rich in Interleukin_2 from the Culture Supernatant 200 liters of supernatant of culture A described in Example 3 were taken, separated, and a fraction rich in IL-2 was concentrated by double ultrafiltration between a first polysulphone membrane having a 100 kDa stop threshold and a second polysulphone membrane having a 10 kDa stop threshold. The operation was performed in the same manner as in Example 5 hereinbefore. The product was 5.6 liters of concentrated aqueous solution of IL-2.

2. Isolation of Glycosylated Interleukin_2 a) Cation Exchange Chromatography

The chromatographic support was a gel based on strong cation-exchange cross-linked agarose, i.e. "S. Sepharose fast flow" said by Messrs PHARMACIA.

The solution obtained in the preceding stage was adjusted to pH 5.5 by adding acetic acid, and its conductivity was adjusted to 5 mS by dilution. The solution was then injected into the column, which was then successively washed with different aqueous solutions (pH 5.5, molarity 50 mM) of ammonium acetate and increasing ionic force of sodium chloride. The glycosylated IL-2 was eluted with a 180 mM solution of of sodium chloride, giving 5.76 liters of an aqueous solution of glycosylated IL-2.

b) Hydrophobic Interaction Chromatography

The chromatographic support was a hydrophobic interaction gel based on hydrophilic polyvinyl resin, i.e. "Butyl Fractogel 650 (M)" said by Messrs MERCK, and placed in a column 50 mm in diameter.

Ammonium acetate up to a molarity of 1.6M was added to the previously-obtained solution of glycosylated IL-2, ammonia was added to adjust the pH to 6.5, and the solution was injected into the column, which had previously been balanced with buffer A, i.e. an aqueous solution (pH 6.5, molarity 1.6M) of ammonium acetate. Under these conditions the glycosylated IL-2 was retained on the chromatographic support. The column was washed with buffer A to eliminate the non-retained products. The column was eluted with buffer B, i.e. a solution of ammonium acetate (pH 6.5, molarity 0.65M).

The product was 1.36 liters of aqueous solution of glycosylated IL-2.

c) Exclusion Chromatography

The chromatographic support was a gel based on cross-linked dextran, i.e. "Sephacryl S 200 HR" said by Messrs PHARMACIA.

The solution obtained at the end of step b) was concentrated on a cellulose acetate membrane, i.e. the YM 10 membrane sold by Messrs AMICON and having a stop threshold of 10 kDa. The solution was then injected into the column, which had first been balanced with an aqueous solution (pH 6.5, molarity 0.1M) of sodium phosphate. The glycosylated IL-2 was then eluted with the last-mentioned solution.

3. Demonstration of Purity of the Product

Electrophoresis on polyacrylamide PAGE-SDS (sodium dodecyl sulphate) gel in the presence of a reducer (dithiothreitol) by the method of LAEMMLI (U.K. LAEMMLI, Anal. BIOCHEM. 78, 1977) followed by dyeing with silver by the method of MERRIL (C. R. MERRIL, Proc. Nat. Acad. Sci. USA, Vol. 76, page 4335, 1979) showed that the purity of the glycosylated IL-2 was greater than 99%.

EXAMPLE 8

In Vitro Activity of Glycosylated Interleukin-2 on Human Lymphocytes

Comparative study of glycosylated interleukin_2 and recombinant interleukin_2 derived from E. coli in the production of LAK cells.

The tests described in this and the following examples were made with recombinant glycosylated IL-2 produced by strain 109.27, isolated as described in Example 5. This product will usually be called glycosylated IL-2, or glycosylated IL-2 ($N_1+N_2$) if there is a risk of confusion.

1. The Importance in Cancer Research of the Study of the Production of LAK Cells in Vitro Adoptive immunotherapy is a new therapeutic approach to cancer, the aim being to amplify the immunological defence reactions of the host against the tumour.

Human peripheral-blood leucocytes, when cultivated in the presence of IL-2, are given a powerful cytotoxic capacity against tumour cells. The effective cells are called LAK ("Lymphokine Activated Killers") (M. T. LOTZE et al (1981) Cancer. Res., 41, 4420–4426). The action of the LAK cells is directed against all kinds of tumours, including freshly-sampled tumour cells. They do not have any activity against normal cells. LAK cells are functionally defined as any cell which, after stimulation by IL-2, develops restricted non-MHC ("Major Histocomptability Complex") cytotoxicity, directed inter alia against tumour cells resistant to the action of NK ("Natural Killer") cells, without previous antigen sensitisation. This definition clearly distinguishes LAK cells from NK cells (i.e. spontaneously cytotoxic without activation by IL-2) and cytotoxic T cells, the action of which is restrained MHC and requires preliminary sensitisation by the target (J. E. TALMADGE et al. (1986) Cancer Treat. Rep., 70, 171–1982).

Recent work suggests that in reality, LAK cells are probably NK cells potentiated by IL-2 and that the LAK precursors are in fact derived from "large granular lymphocytes" (K. ITOH et al (1986) J. Immunol., 136, 3910–3917).

Interleukin–2 generates LAK cells not only in vitro but also in vivo. The capacity of a particular IL-2 to generate LAK cells in vitro is therefore an important indication of its potential anti-tumour activity.

2. Experimental Method a) The following kinds of interleukin-2 were tested:
Glycosylated IL-2 ($N_1+N_2$)
Glycosylated IL-2 ($N_2$), obtained by subjecting the fraction 1 isolated during step 2b of Example 5 to steps c) and d) thereof;
Non-glycosylated IL-2 (M) obtained by subjecting fraction 3 isolated during step 2b of Example 5 to steps c) and d) thereof, and
Recombinant IL-2 derived from *E. coli*, hereinafter sometimes abbreviated to IL-2 coli, prepared as described hereinafter.

The gene coding for IL-2 was transfected into *E. coli* cells and expressed at high rates. After solubilisation, renaturation and purification by reverse-phase HPLC chromatography and exclusion chromatography by the method described by Liang et al (S. I. Liang et al., (1985) Biochem. J. 229, 429–439), the recombinant protein had a specific activity of $5-10\times10^5$ U/mg.

b) Preparation of the Lymphocytes

The culture medium consisted of RPMI 1640 (Gibco-BRL) plus 10% AB human serum (CTS Purpan, Toulouse, France) inactivated by heat (1 hour at 56° C.), 2 mM sodium pyruvate, 5 mM HEPES, 4 mM L-glutamine, 100 U/ml penicillin, 100 µg/ml streptomycin and 0.25 µg/ml amphotericin B (this medium will hereinafter be called complete medium).

The blood from a healthy patient was sampled under aseptic conditions.

The peripheral lymphocytes were separated from the erythrocytes and granulocytes by centrifuging on a Ficoll-Hypaque (PHARMACIA) gradient by the method described by A. Boyum in "Methods in enzymology" (G. Di Sabato, J. J. Langone, H. Van Vunakis, ed.), Vol. 108, page 88, Academic Press, Inc., 1984.

The lymphocytes were washed three times in complete medium.

The adhesive cells (monocytes and macrophages) were eliminated by adhesion to plastic: the cells were suspended in the complete medium in a concentration of 5 to $10\times10^5$ per ml and seeded in culture flasks at a density of $1-2\times10^5$ cells per cm². The flasks were placed in the presence of 5% $CO_2$ at 37° C. for 1 hour, after which the non-adhesive lymphocytes were recovered by suction after gentle agitation of the culture flasks.

c) In Vitro Cultivation of Lymphocytes in the Presence of IL-2

The non-adhesive lymphocytes isolated in the previous paragraph were washed once and cultivated et a concentration of $10^5$ cells per ml in complete medium in the presence of various concentrations of each of the two tested forms of IL-2 (100, 30, 10 and 1 U/ml) at 37° C. and in the presence of 5% CO2 for 48 hours. The cells were then washed. They are hereinafter considered as effective cells.

d) Demonstration of Cytotoxic Activity

The cytotoxic activity of the effective cells was evaluated after 4 hours of contact with target cells of the human T lymphoid line C8166-45/C63 described by S. Z. Salahuddin et al. (Virology 129, 51–64, (1983) and Science 223, 703–707, (1984)) resistant to NK type cytoxicity. This line will hereinafter be called line HT1. $6\times10^5$ target cells were radio-tagged with 200 µCi of $^{51}$Cr (sodium chromate, Amersham) at 37° C. for 1 hour in a volume of 0.4 ml of complete medium without serum, and were then washed several times. The target cells ($10^4$ in a volume of 0.1 ml of complete medium) and the effective cells in a volume of 0.1 ml of complete medium were distributed in round-bottomed microtitration plates (Falcon) with varying ratios of effective cells to target cells (50:1, 10:1, 1:1). The microtitration plates were centrifuged and, after incubation at 37° C. for 4 hours in the presence of 5% $CO_2$, the supernatant from each well was recovered and the radioactivity was measured using a gamma counter. The cytotoxicity was determined from the quantity of $^{51}$Cr released by the dead target cells. The non-specific cytotoxicity was determined from the amount of radioactivity spontaneously released by the target cells in the absence of effective cells. The maximum cytotoxicity was determined from the quantity of radioactivity released by the target cells in the absence of effective cells and in the presence of 1N hydrochloric acid. Each experimental point is threefold (sixfold in the determination of non-specific and maximum cytotoxicity) and the percentage of specific lysis is calculated as the average plus or minus the standard deviation in accordance with the following formula:

$$\text{Percentage of specific lysis}$$
$$\frac{\text{cpm of experimental wells} - \text{non-specific cpm}}{\text{maximum cpm} - \text{non-specific cpm}} \times 100$$

The procedure described in paragraphs b), c) and d) hereinbefore was followed in the case of glycosylated IL-2 ($N_2$) and non-glycosylated IL-2 (M). A slightly different method described by H. D. Engers (H. D. Engers et al. (1986) Methods of enzymology, 132, 437–457) was followed in the case of ($N_1+N_2$) glycosylated IL-2 and IL-2 coli, which were tested with target cells from the HT1, Daudi and Jurkatt lines, all resistant to NK lysis.

3. Results

The results are collected in Tables 3 and 4 hereinafter.

TABLE 3

Cytolytic activity against HT$_1$ line of LAK cells generated from healthy donor by non-glycosylated IL-2 (M) and glycosylated IL-2 (N2)

| Doses of IL-2 CTLL-2 activity | Ratio of effective cells to target cells | Percentage specific lysis with non-glycosylated IL-2 (M) | Percentage specific lysis with glycosylated IL-2 (N$_2$) |
|---|---|---|---|
| 1 000 U/ml | 50/1 | 43.6 ± 1.2 | 53.9 ± 1.6 |
|  | 10/1 | 24.1 ± 0.6 | 36.3 ± 3.2 |
|  | 1/1 | 6.5 ± 7.9 | 33.4 ± 2.4 |
| 100 U/ml | 50/1 | 30.9 ± 2.6 | 40 ± 6.1 |
|  | 10/1 | 13.7 ± 1.8 | 15.4 ± 2.8 |
|  | 1/1 | 0 | 5.6 ± 4.1 |
| 10 U/ml | 50/1 | 11.3 ± 1.7 | 23 ± 3.9 |
|  | 10/1 | 0 | 7.1 ± 2.2 |
|  | 1/1 | 0 | 2.9 ± 4.2 |
| 1 U/ml | 50/1 | 0 | 7.8 ± 3.9 |
|  | 10/1 | 0 | 8.5 ± 3.8 |
|  | 1/1 | 0 | 0.4 ± 0.8 |

TABLE 4

Cytolytic activity against Daudi, HT$_1$ and Jurkatt lines, of LAK cells generated by a number of kinds of Interleukin-2, using lymphocytes from healthy donors.

| Target cells |  | Concentration of IL-2 | |
|---|---|---|---|
|  |  | 20 U/ml | 50 U/ml |
| Daudi | IL-2 coli | 1* | 1* |
|  | IL-2 glycosylated (N$_1$ + N$_2$) | 3.12 | 1.1 |
| HT$_1$ | IL-2 coli | 1 | 1 |
|  | IL-2 glycosylated (N$_1$ + N$_2$) | 8 | 1.9 |
| Jurkatt | IL-2 coli | 1 | 1 |
|  | IL-2 glycosylated (N$_1$ + N$_2$) | 2.7 | 0.95 |

$$\text{Index of activity} = \frac{\text{percentage lysis obtained with IL-2 coli}}{\text{percentage lysis obtained with glycosylated IL-2}}$$

Table 3 shows the following in the case of target cells from the HT$_1$ line:

The superiority of glycosylated IL-2 (N$_2$) at concentrations of IL-2 lower than 1000 U/ml;

This superiority increases when the ratio of effective cells to target, cells decreases;

This superiority decreases at high proportions of IL-2 (1000 U/ml) and/or when the ratio of effective cells to target cells is high.

Table 4 shows the following in the case of target cells from the Daudi, HT$_1$ and Jurkatt lines:

The superiority of glycosylated IL-2 compared with IL-2 coil at a concentration of 20 U/ml IL-2;

This superiority decreases when the concentration of IL-2 increases.

These studies show that:

glycosylated IL-2 generates LAK cells active against three tumour lines;

This LAK activity is obtained with lower concentrations with glycosylated IL-2 than with IL-2 coli;

The activity of LAK cells generated by glycosylated IL-2 is greater than the activity of LAK cells generated by IL-2 coli in the following two situations:

Low concentration of IL-2

Unfavourable ratio of effective cells to target cells (below 10/1 ).

These results are particularly promising as regards clinical use of glycosylated IL-2, since these studies show that this form of IL-2 can be used in lower concentrations than IL-2 coli to give a similar anti-tumour effect. This should substantially reduce the toxicity associated with administration of the product.

EXAMPLE 9

Immunomodulating Activity of Glycosylated Interleukin—2: Stimulation of the Immune Response to Humoral Mediation in the Mouse a) Aim of the study This study was motivated on the one hand because it has been shown that IL-2 stimulates in vivo a polyclonal immunoglobulin M response (hereinafter abbreviated to IgM) in non-immunised mice and a specific IgM response in immunised mice C. M. Wegand (1986), J. Exp. Med. 163, 1607–1612) and, secondly, that IL-2 coli in vitro is capable of inducing differentiation of activated B lymphocytes on human cells (T. A. Waldmann et al. (1984), J. Exp. Ned. 160, 1450–1466). The aim of the study is to evaluate the in vivo activity of glycosylated interleukin 2 in stimulating the immune response to humoral mediation in the BALB/C mouse, by measuring the primary splenic response to immunisation with a thymo-dependent, antigen (ovalbumin).

b) Experimental Procedure

α) Animals—Environmental Conditions

Species: BALB/C mouse

Acclimatisation: the animals were acclimatised for a week before the beginning of treatment Number of animals: 90 females Weight of animals at beginning of study: about 20 g Food: The animals were supplied on demand with complete composite food A04.c, sold by Messrs V.A.R.

Water: Tap water was supplied on demand, via an automatic system.

Environmental conditions:

Temperature 22° C. (±2° C.)

Humidity 60% (±10%)

Photo-period 12/24 h

Habitat: The animals were kept in stainless-steel cages. They were distributed in cages containing 5 individuals, in groups of 15 from the same batch.

β) Treatment of the Animals

The animals were immunised with ovalbumin having 98% electrophoretic purity (sold by Messrs SIGMA, reference A-5378) on day 1 of the study, by an intraperitoneal dose of 50 μg of ovalbumin dissolved in 0.5 ml of sterile PBS buffer (Phosphate Buffer Saline) per mouse. Ovalbumin (molecular weight 40,000, 5 known antigenic determinants) was chosen as antigen because it is a xenogenic protein having good immunogenicity.

Glycosylated IL-2, isolated as described in Example 5, was intraperitoneally administered on days 2, 4, 6 and 8 in normal BALB/C mouse serum diluted to 1:80 in PBS buffer. The presence of proteins in the serum does not significantly influence the immune system but avoids any loss of IL-2 through non-specific adsorption on the walls of tubes or syringes. The following Table gives the doses administered to the various belches of 15 mice.

| Batch No | Dose administered (U/kg) | Volume administered |
|---|---|---|
| 0 | vehicle | 0.5 ml/mouse |
| 1 | IL-2/7.5 $10^4$ | 0.5 ml/mouse |
| 2 | IL-2/3.75 $10^5$ | 0.5 ml/mouse |
| 3 | IL-2/1.88 $10^6$ | 0.5 ml/mouse |
| 4 | IL-2/9.38 $10^6$ | 0.5 ml/mouse |
| 5 | IL-2/4.69 $10^7$ | 0.5 ml/mouse |

The animals were killed on day 9.

γ) Measurements Made

After the dead animals had been weighed, their spleens were removed under sterile conditions and were weighed and mechanically crushed. The crushed material was filtered on sterile gauze in order to eliminate all conjunctivo-adipose aggregates, and was centrifuged at 400 g for 10 minutes. The splenocytes were suspended and washed three times. After washing, a number of counts were made in order to calculate the total number of splenocytes per animal and distribute them at the desired cell concentration. The splenocytes were cultivated for 96 hours in 5 ml wells made of polystyrene plates, containing $2 \times 10^5$ living splenocytes per ml of culture medium, which contained 10% foetal calf serum (medium RPMI, 1640 sold by Messrs BIOPRO).

The various kinds of anti-ovalbumin IgM were then determined by radioimmunometry as follows:

Adsorption of ovalbumin on PVC plate (100 μl per well of a 50 μg/ml solution in a 0.1M, pH 7.5 phosphate buffer), 18 hours at +4° C.

After washing the wells with 0.1M, pH 7.5 phosphate buffer, the wells were saturated for 1 hour at 37° C., with 200 μl of a solution of 1% Tween 20 surfactant (v/v) in 0.1M, pH 7.5 phosphate buffer.

After the wells had been washed, incubation of the culture supernatant to be determined (100 μ"l per well) diluted to ½ in 0.1M, pH 7.5 phosphate buffer with 0.1% (p/v) of gelatin and 0.1% (v/v) of Tween 20 surfactant, 18 hours at +4° C.

After the wells had been washed, incubation with 100 μl per well of polyclonal anti-mouse IgM goat antibody (sold by Immunotech, reference 115-0575) radio-tagged with iodine 125 (7.5 ½Ci/½g, 250,000 cpm/100 μl, 3 hours at +37° C.).

After the wells had been washed with a solution (0.9% NaCl (p/v), 0.1% Tween 20 (v/v)), the fixed radioactivity was measured using a gamma counter.

The various measurements hereinbelow, made on each mouse, were used in the case of each batch of mice, i.e. each dose administered, to calculate the average weight of the spleen relative to body weight, the average total number of splenocytes per animal and the average quantity of anti-ovalbumin IgM produced by the splenocytes, the latter quantity being proportional to the radioactivity.

c) Results

Figure 6:
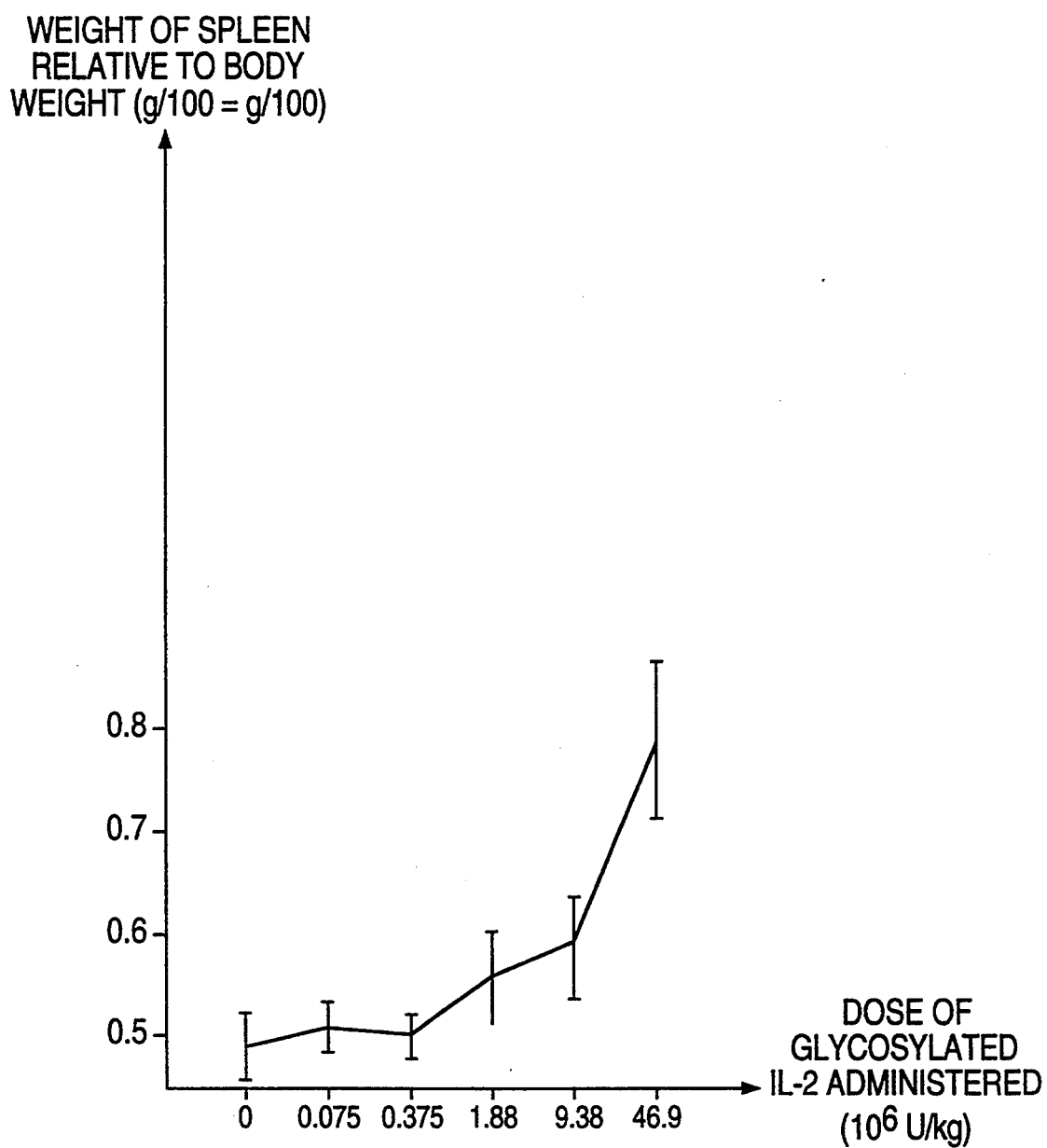
Figure 7:
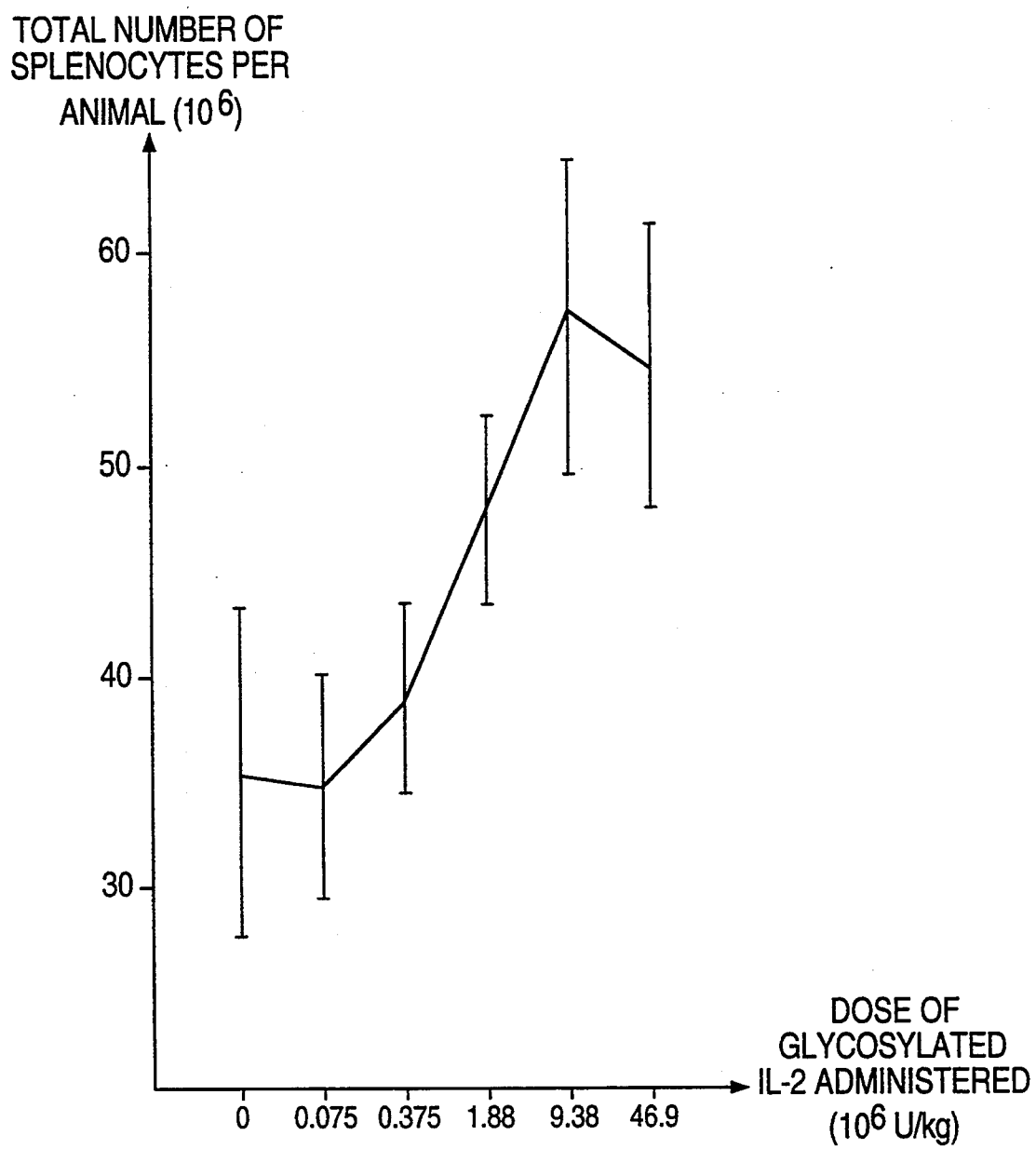

The results are shown in FIGS. 6, 7 and 8. Our comments are as follows:

Starting from a dose of $1.88 \times 10^5$ U/kg (i.e. 37 500 U per mouse), glycosylated IL-2 produces a more than 50% relative increase in the weight of the spleen and the total number of splenocytes per animal. It has also been shown by tests (not given here) that the total T lymphocytes increase more in proportion than the others (20%).

A dose higher than $1.88 \times 10^6$ U/kg significantly increases the quantity of specific kinds of IgM produced by each plasmocyte.

The glycosylated IL-2 therefore has considerable immunostimulating activity.

EXAMPLE 10

Anti-Tumour Activity of Glycosylated Interleukin-2: Immunotherapy of Cancer in the Mouse a) Experimental Method The study was made on DBA/2 mice distributed in batches of 5. On day 0, $0.2 \times 10^4$ syngenic cells of lymphosarcoma SL2 were intraperitoneally injected into the mice.

In a first set of experiments, various doses of glycosylated interleukin—2 isolated as described in Example 5 (0, 8, 40, 200, 1000 and 5000 U per day) were injected in mice of 6 different batches of 5 on days 3–7 and 10–14. The number of mice surviving each day was counted during a period of 30 days. This first set of experiments showed anti-turnout activity of glycosylated interleukin—2 administered at a dose of 5000 U per day.

In a second set of experiments, the dose administered was fixed at 5000 U in days 10 to 14 and variations were made in the doses administered previously and in the days when they were administered.

b) Results.

The results of the second set of experiments are shown in Table 5 hereinafter and illustrated in FIG. 9, which shows the number of mice surviving during a 30-day period in batches 0, 1, 2 and 3 in Table 5.

TABLE 5

| Batch | Administered dose of glycosylated interleukin-2 (U/day) | | Mice survivings after 30 days |
|---|---|---|---|
| 0 Control | 0 | days 10–14 0 | 0/5 |
| 1 | days 3–7 100 | days 0–14 5 000 | 4/5 |
| 2 | 0 | days 10–14 5 000 | 3/5 |
| 3 | days 5–7 100 | days 0–14 5 000 | 5/5 |

These results are a very clear indication of the considerable anti-tumour activity of glycosylated interleukin—2.

EXAMPLE 11

Toxicological Study of Glycosylated Interleukin-2 in the Mouse a) Aim of the study It has been shown that the main toxic effect of recombined IL-2 (produced in *E. coli*) administered to man or to the mouse, either alone (M. Rosenstein et al., (1986) J. Immunol., 137, 1735-1742) or with LAK cells (S. E. Ettinghausen (1988) J. Natn Cancer Inst. 80, 3, 177–188) is extravasation of intravascular liquid, i.e. retention of this liquid in certain organs (thymus, spleen, lungs, liver and kidneys).

Accordingly, the aim of this study is to evaluate the toxicity, if any, of glycosylated interleukin 2 by way of retention of intravascular liquid in the BALB/C mouse when administered intraperitoneally three times a day for 3 days and 6 days.

b) Experimental Procedure

Experimental procedure was similar to that described by M. Rosenstein (M. Rosenstein et al. (1986) J. Immunol, 137, 1735-1742).

α Animals—Environmental Conditions
Species: BALB/C mice
Age of animals at beginning of study: about 4 weeks
Acclimatisation: 1 week
Number of animals: 120 females
Weight of animals at beginning of study: 20 g
Method of identification: tagging of ears
Food: complete AO4C food, sold by Messrs V.A.R., on demand
Water: tap water on demand
Environmental conditions>
  Temperature: 22° C. (±2° C.)
  Humidity: 60% (±10%)
  Photo-period: 12/24 h.
Habitat: stainless steel cages. The animals were divided into groups of 12 from the same batch.

β) Treatment of Animals

Glycosylated IL-2, isolated as described in Example 5, was intraperitoneally administered three times a day (morning, midday and evening) for three days to batches 0, 2, 3, 4 and 5 and for six days to batches 1, 6, 7, 8 and 9, in normal BALB/C mouse serum diluted to 1:80 in PBS buffer (Phosphate Buffer Saline). The volume administered was 0.5 ml.

The following Table gives the doses administered to the various batches of 12 mice.

TABLE

| BATCH | Dose of glycosylated IL-2 per administration | | Total dose administered |
|---|---|---|---|
| | $10^3$ U | $10^3$ U/kg | $10^3$ U/kg |
| 0 | 0.000 | 0.000 | 0.000 |
| 1 | 0.000 | 0.000 | 0.000 |
| 2 | 3.250 | 162.5 | 1462.5 |
| 3 | 12.500 | 625 | 5625.00 |
| 4 | 50.000 | 2.500 | 22500 |
| 5 | 200.000 | 10.000 | 90.000 |
| 6 | 3.250 | 162.5 | 2925.000 |
| 7 | 12.500 | 625 | 11.250 |
| 8 | 50.000 | 2500 | 45.000 |
| 9 | 200.00 | 10000 | 180.000 |

The animals in batches 0, 2, 3, 4 and 5 were killed at the end of the 4th day, whereas the animals in batches 1, 6, 7 and 8 were killed on the 7th day.

γ) Practical Examinations
Clinical examination;

The animals were observed every day during the entire study.

The examinations described hereinafter were made only on the first six animals of each batch.
Examination on autopsy (days 4 and 7)
The mice were anaesthetised with pentobarbitone.
Blood tests
During autopsy, blood samples were taken for biochemical analysis from the abdominal aorta.
Anatomical study
The liver, spleen, kidneys, thymus and lungs were taken and weighed in order to detect any toxicity involving retention of fluid.

Measurement of weight when fresh: the organs were weighed in lyophylisation flasks; each flask (one per animal and per organ) was first weighed before inserting the organ.

Determination of dry weight: the organs were frozen at −80° C. then freeze-dried for 4 days in a lyophiliser.

Special examinations

The examinations were made on the last six animals of each batch. On day 4 in the case of batches 0, 2, 3, 4 and 5 and on day 7 in the case of batches 1, 6, 7, 8 and 9, the mice were intraveneously given two microcuries of bovine serum albumin radio-tagged with iodine 125 (specific activity of 5 microcuries per mg).

Two hours after injection, the mice were killed and the lungs, kidneys, liver, thymus and spleen were taken, weighed and placed in 5 ml PVC tubes, so that the radioactivity of each organ could be measured with the gamma counter.

The radio-iodine bovine serum albumin can be considered as a label showing extravasation of intravascular liquid (1). Thus, if an organ x of a mouse treated with IL-2 is more radioactive than an organ of a control mouse, it may be that IL-2 affects the retention of intravascular liquid in the organ under consideration.

c) Results
Clinical examinations

The behaviour of the animals did not change and no death was recorded.
Blood tests Evaluation of the biochemical parameters (total proteins, albumin, triglycerides, urea and creatinine) did not show any problems of liver or renal toxicity.

Comparative Study of the Fresh and Dry Weight of the Thymus, Liver, Lungs, Spleen and Kidneys The fresh weight of the thymus and kidneys did not increase after 3 or 6 days of treatment, irrespective of the doses of IL-2.

There was a marked increase in the fresh weight of the spleen, lungs and liver, particularly after 6 days of treatment the percentage dry weight to fresh weight does not vary: this means that the proportion of water in these organs remained constant and represents a lymphoid hyperplasia inherent in the pharmacological activity of IL-2.

Kinetic Study of Extravasation, if any, induced by IL-2, Using Radio-tagged Albumin There was no significant variation in the proportion of bovine serum albumin, tagged with iodine 125, in the organs under study, i.e. the thymus, liver, lungs, spleen and kidneys, irrespective of the dose and duration of treatment, and there was very little change in the spleen.

d) Conclusion

The toxicological study made on the BALB/C mouse showed the absence of appreciable toxic effects of glycosylated IL-2. More particularly, following the test method used by M. Rosenstein, it showed the absence of extravasation of intravascular liquid, as described in the case of IL-2 coli.

EXAMPLE 12

Toxicological Study of Glycosylated Interleukin_2 in the Rat a) Aim of the study The aim of this study was to evaluate the toxicity, if any, of glycosylated IL-2, more particularly the formation of oedemas in the Sprague Dawley rat.

b) Method of Experiment

Glycosylated interleukin_2 isolated as described in Example 5 was intraperitoneally injected into batches of 6 rats (3 males and 3 females) in doses of 2 million, 10 million and 50 million UI/kg per day (i.e. 0.1, 0.5 and 2.5 mg/kg per day) for 3 days. At the same time the animals were orally given sodium chloride in doses of 1 g/kg per day.

On the 3rd day the animals were orally given an excess of 10 mg/kg of water and were then placed in a metabolism cage in order to measure diuresis during 24 hours.

Each batch was compared with an untreated control batch and a batch treated with sodium chloride only.

c) Results

No clinical anomaly was observed.

The animals were weighed before the beginning of the study and then on days 3 and 4. No difference between the batches was observed.

The blood tests (haematocrit, urea, creatinine, total proteins, albumin, cholesterol, triglycerides, GPT, LDH, sodium, potassium, chlorides and calcium) made on day 4 showed a slight reduction of plasma albumin and proteins with effective dose.

The study of urinary elimination, as follows:

Volume

Semi-quantitative examination using reactive strips (pH, density, proteins, glucose, ketones, bilirubin, blood and urobilinogen)

Determination of sodium ions, potassium, chlorides and creatinine did not show any anomaly.

Some organs (liver, spleen, kidneys and thymus) showed a slight increase in the weight of the spleen per effective dose.

The autopsy did not show any macroscopic lesions.

An examination under an optical microscope showed that IL-2 induced activation of the lymphoid system, as follows:

Very slight hyperplasia of the periarteriolar lymphoid sleeves and marginal splenic zones in three animals treated with a dose of $50 \times 10^5$ Ul/kg/day, and More frequent ganglian plasmocytosis in the treated animals, but without effective dose.

d) Conclusion

This toxicological study of Sprague Dawley rats showed the absence of appreciable toxic effects of glycosylated IL-2 at a dose 5 times greater (2.5 mg/kg/day compared with 0.5 mg/kg/day) than the lethal dose observed by Y. HARADA (Y. Harada (1987), Preclincal Safety of Biotechnology Products intended for human use—p. 127–142—Alan R. Liss. Inc.) with IL-2 coli.

Glycosylated IL-2 is therefore much less toxic than IL-2 coli, in both the mouse and the rat.

EXAMPLE 13

Experimental Galenic Formulation of Glycosylated Interleukin-2 a) Methods of experiment

Experimental freeze-drying of an aqueous solution of sodium phosphate, pH 6.5, containing glycosylated IL-2 obtained as described in Example 5 were made in the presence or absence of various excipients, present in variable proportions. The solute was then reconstituted, its appearance was observed, its pH was measured, and the quantity of glycosylated IL-2 present, was determined by HPLC on a reverse phase column (compare Example 5-3 ) and the CTLL-2 activity was measured. These operations were made immediately after freeze-drying after the substance had been preserved for one year at a temperature of 4° C., and after preservation for three months at a temperature of 25° C. and after preservation for three months at a temperature of 37° C.

b) Results

If an aqueous solution of sodium phosphate containing 80 µg/ml of glycosylated IL-2 without excipient is freeze-dried, and if the solute is immediately reconstituted by adding water for injectable preparation, the result is a clear colourless solution containing more than 80% of the initial CTLL-2 activity. After the freeze-dried material has been preserved for six months, the reconstituted solution contains about 50% of the initial CTLL-2 activity.

If 10 mg/ml of hydrolysed gelatin (ROUSSELOT Ref. DSF), 1 mg of polyethylene glycol, average molecular weight 6000 (HOECHST Ref. DAB 8) or 10 mg/ml human serum albumin (SIGMA Ref. 3782) are added during freeze-drying to an aqueous solution of sodium phosphate containing 80 µg/ml of glycosylated IL-2 having a specific CTLL-2 activity near $18 \times 10^5$ U/mg, and if the freeze-dried material is preserved at 4° C., for 1 year and the solute (clear and approximately at pH 6.5) is reconstituted, the results of chromatographic analysis (accuracy about 3%) are as follows:

More than 90% in the case of polyethylene glycol and 100% in the case of hydrolysed gelatin and human serum albumin In all cases with a specific CTLL-2 activity of near $18 \times 10^5$ U/mg (of IL-2 determined by HPLC). In the case of these last two excipients, therefore, the CTLL-2 activity per ml of solute remained identical to its initial value.

If 10 mg/ml of hydrolysed gelatin (ROUSSELOT Ref. DSF) and 10 mg/ml of apyrogenic alanine (AJINOMOTO) are added during feeeze-drying to an aqueous solution of sodium phosphate containing 450 µg/ml of glycosylated IL-2 having a specific CTLL-2 activity of near $18 \times 10^5$ U/ml, the resulting freeze-dried substance has a water content of less than 3%. After the freeze-dried material has been preserved at 4° C. for 3 months, the reconstituted solute is clear and has a pH of about 6.5 and chromatographic analysis (accuracy about 3%) shows 100% of the initial glycosylated IL-2 with a specific CTLL-2 activity near $18 \times 10^5$ U/mg (of IL-2 determined by HPLC).

The foregoing results show that, after freeze-drying, glycosylated IL-2 has excellent stability for acceptable pharmaceutical formulations. Probably the freeze-dried material can be preserved for several years at a temperature of 4° C. It is also found that in all cases the reconstituted solute is clear and at a physiological pH without adding a toxic agent or chemically modifying the molecule to make it soluble. These properties of glycosylated IL-2 differ from *E. coli* derived IL-2. The latter substance loses more than 50% of its activity and gives opalescent solutions after freeze-drying (see European Patent Application No. 0 158 487, page 10). To soluble therefore, it is necessary to add toxic solubilising agents such as SDS (Sodium Dodecyl Sulphate).

The skilled addressee, after reading the preceding description, will understand the importance of glycosylated IL-2 as a drug, and its numerous advantages compared with non-glycosylated IL-2, e.g. derived from *E. coli*—i.e. the possibility of using smaller doses to give the same activity and better tolerances at large doses owing to lower toxicity, lower immunogenicity, solubility in an aqueous solvent at a physiological pH without adding a toxic solubilising agent or chemical modification of the molecule, and excellent stability after lyophylisation in pharmaceutically acceptable formulations.

It is claimed:

1. A purified interleukin-2 preparation suitable for use as a pharmaceutical, consisting essentially of disialilated glycosylated interleukin-2, monosialilated glycosylated interleukin-2, or a mixture thereof, and which is without a toxic solubilizing agent.

2. The interleukin-2 preparation of claim 1, wherein the purity of said preparation is greater than 99% when said preparation is subjected to electrophoresis on polyacrylamide gel in the presence of SDS.

3. The interleukin-2 preparation of claim 2, wherein said purity is greater than 99.5%.

4. The interleukin-2 preparation of claim 1, wherein said preparation has a specific CTLL-2 activity that is greater than $15 \times 10^6$ U/mg.

5. An interleukin-2 preparation according to claim 1, characterised in that the glycosylated interleukin-2 can be used to obtain a clear reconstituted solution at a physiological pH after lyophilisation of an aqueous solution containing it at pH 6.5 and immediate reconstitution of the solute.

6. An interleukin-2 preparation according to claim 1, characterised in that the glycosylated interleukin-2 retains its initial CTLL-2 activity after lyophilisation in an aqueous solution of pH 6.5 to which hydrolysed gelatin or human serum albumin has been added, preservation of the lyophilised product at a temperature of 4° C. for one year, and reconstitution of the solute.

7. An interleukin-2 according to claim 1, characterised in that the glycosylated interleukin-2 retains its initial CTLL-2 activity after lyophilisation in an aqueous solution of pH 6.5 to which hydrolysed gelatin and alanine have been added, preservation of the lyophilised product at a temperature of 25 ° C. for 3 months, and reconstitution of the solute.

8. An interleukin-2 preparation according to claim 1, characterised in that the glycosylated interleukin-2 retains its initial CTLL-2 activity after lyophilisation in art aqueous solution of pH 6.5 to which hydrolysed gelatin and alanine have been added, preservation of the lyophilised product at a temperature or 37° C. for 3 months, and reconstitution of the solute.

9. A pharmaceutical composition, comprising an interleukin-2 preparation according to claim 1, and a pharmaceutically acceptable excipient.

10. A pharmaceutical composition according to claim 9, characterised in that said pharmaceutically acceptable excipient contains hydrolysed gelatin and alanine.

11. A method of stimulating immunity in a patient comprising the step of administering to said patient a therapeutically effective amount of a pharmaceutical composition according to claim 9.

12. In a method of treating a patient having a condition susceptible to a treatment with a composition containing interleukin-2, the improvement wherein said composition containing interleukin-2 is a pharmaceutical composition according to claim 9.

13. An interleukin-2 preparation according to claim 1, which is made according to a process comprising the steps of
    (a) isolating a fraction rich in interleukin-2 and glycosylated interleukin-2 from a cell culture of recombinant Chinese hamster ovary cells,
    (b) contacting the isolated fraction rich in interleukin-2 and glycosylated interleukin-2 from step (a) with a cation exchange chromatographic medium, and collecting an eluate containing glycosylated interleukin-2 therefrom,
    (c) contacting the eluate from step (b) with a hydrophobic interaction chromatograph, and collecting an eluate containing glycosylated interleukin-2 therefrom, and
    (d) contacting the eluate of step (c) with an exclusion chromatograph, and collecting an eluate containing glycosylated interleukin-2 therefrom, wherein the eluate obtained from step (d) consists essentially of disialilated ($N_2$) glycosylated interleukin-2, monosialilated ($N_1$) glycosylated interleukin-2 or a mixture thereof.

14. An interleukin-2 preparation according to claim 13, characterized in that said cell culture has been cultivated in a synthetic medium.

15. An interleukin-2 preparation according to claim 14, characterised in that the synthetic medium contains polyvinyl pyrrolidone.

16. An interleukin-2 preparation according to claim 13, wherein in step (a) of said process, said cell culture of recombinant Chinese Hamster Ovary cells is transformed with a vector containing a DNA sequence coding for a natural precursor of human interleukin-2.

17. An interleukin-2 preparation according to claim 13, wherein step (a) of said process comprises filtering a supernatant from said cell culture between a first membrane having a stop threshold between 30–150 kDa, and filtering said supernatant between a second membrane having a stop threshold between 5–10 kDa, and collecting a fraction rich in interleukin-2 and glycosylated interleukin-2.

18. An interleukin-2 preparation according to claim 13, wherein step (b) of said process further comprises a step of adjusting the pH of said fraction rich in interleukin-2 and glycosylated interleukin-2 from step (a) to an adjusted pH between 4.5 and 6.5.

19. An interleukin-2 preparation according to claim 18, wherein said adjusted pH is between 5.2 and 5.7.

20. An interleukin-2 preparation according to claim 13, said process further comprising, prior to collecting an eluate in steps (b)–(d), the step of eluting with an aqueous solution without a toxic solubilizing agent.

21. An interleukin-2 preparation according to claim 13, said process comprising the steps of:
    (a) isolating a fraction containing interleukin-2 and glycosylated interleukin-2 from a cell culture of Chinese hamster ovary cells,
    (b) adjusting said fraction from step (a) to a pH between 4.5 and 6.5, contacting the adjusted fraction with a cation exchange chromatographic medium, eluting with a solution having a pH between 4.5 and 6.5, collecting therefrom an eluate containing disialilated ($N_2$) glycosylated interleukin-2, monosialilated ($N_1$) glycosylated interleukin-2 or a mixture thereof,
    (c) adjusting the pH of said eluate from step (b) to between pH 4.5 and 8.0, contacting the adjusted eluate with a hydrophobic interaction chromatographic medium, eluting with a solution having a pH between 4.5 and 8.0, and collecting therefrom an eluate containing disialilated ($N_2$) glycosylated interleukin-2, monosialilated ($N_1$) glycosylated interleukin-2 or a mixture thereof, and
    (d) adjusting said eluate collected according to step (c) to a pH between 5.0 and 8.0, contacting the adjusted eluate with an exclusion chromatographic medium, eluting with a solution having a pH between 5.0 and 8.0, and collecting therefrom an eluate consisting essentially of disialilated ($N_2$)

glycosylated interleukin-2, monosialilated (N₁) glycosylated interleukin-2 or a mixture thereof.

22. An interleukin-2 preparation according to claim 21 wherein in each of steps (b)–(d), said solution used for eluting is an aqueous solution without a toxic solubilizing agent.

23. A pharmaceutical composition comprising an interleukin-2 preparation according to claim 13 and a pharmaceutically acceptable excipient.

24. A pharmaceutical composition comprising an interleukin-2 preparation according claim 21, and a pharmaceutically acceptable excipient.

25. An interleukin-2 preparation according to claim 13, wherein said process further comprises, in step (b), prior to contacting the isolated fraction rich in interleukin-2 and glycosylated interleukin-2 from step (a) with said cation exchange chromatographic medium, contacting said fraction with an anion exchange chromatographic medium.

* * * * *

UNITED STATES PATENT AND TRADEMARK OFFICE
CERTIFICATE OF CORRECTION

PATENT NO. : 5,417,970
DATED : May 23, 1995
INVENTOR(S) : Willem ROSKAM et al.

It is certified that error appears in the above-indentified patent and that said Letters Patent is hereby corrected as shown below:

IN THE DRAWINGS

Figure 1, "TRYROSINE" should read --TYROSINE--; and Figure 2, inside the box, please delete lines 5-8.

Signed and Sealed this

Fourteenth Day of May, 1996

Attest:

BRUCE LEHMAN

Attesting Officer   Commissioner of Patents and Trademarks